(12) United States Patent
Williams et al.

(10) Patent No.: US 11,179,294 B2
(45) Date of Patent: Nov. 23, 2021

(54) PRESERVATIVE REMOVAL FROM EYE DROPS

(71) Applicant: TearClear Corp., Copley, OH (US)

(72) Inventors: Michael S. Williams, Keystone Heights, FL (US); Deniz Hay, Gainesville, FL (US)

(73) Assignee: TEARCLEAR CORP., Copley, OH (US)

( * ) Notice: Subject to any disclaimer, the term of this patent is extended or adjusted under 35 U.S.C. 154(b) by 0 days.

(21) Appl. No.: 17/200,595

(22) Filed: Mar. 12, 2021

(65) Prior Publication Data

US 2021/0196569 A1    Jul. 1, 2021

Related U.S. Application Data

(63) Continuation of application No. PCT/US2020/066216, filed on Dec. 18, 2020.

(60) Provisional application No. 62/950,866, filed on Dec. 19, 2019.

(51) Int. Cl.
| | |
|---|---|
| *A61J 1/14* | (2006.01) |
| *A61K 9/00* | (2006.01) |
| *A61K 9/08* | (2006.01) |
| *A61K 47/18* | (2017.01) |
| *B01D 67/00* | (2006.01) |
| *B01D 69/14* | (2006.01) |
| *B01D 71/26* | (2006.01) |
| *B01J 20/26* | (2006.01) |
| *B01J 20/28* | (2006.01) |

(52) U.S. Cl.
CPC ........... *A61J 1/1456* (2015.05); *A61J 1/1475* (2013.01); *A61K 9/0048* (2013.01); *A61K 9/08* (2013.01); *A61K 47/186* (2013.01); *B01D 67/0004* (2013.01); *B01D 69/147* (2013.01); *B01D 71/26* (2013.01); *B01J 20/265* (2013.01); *B01J 20/28016* (2013.01); *B01J 20/28042* (2013.01); *B01J 2220/52* (2013.01); *B01J 2220/56* (2013.01)

(58) Field of Classification Search
CPC ........... A61K 9/00; A61K 9/08; A61K 47/18; B01D 67/00; B01D 69/14; B01D 71/26; B01J 20/26; B01J 20/28
See application file for complete search history.

(56) References Cited

U.S. PATENT DOCUMENTS

| | | |
|---|---|---|
| 3,293,112 A | 12/1966 | Kehr |
| 3,322,711 A | 5/1967 | Bush et al. |
| 4,459,388 A | 7/1984 | Hettche et al. |
| 5,056,689 A | 10/1991 | Heyl et al. |
| 5,064,908 A | 11/1991 | Schuster et al. |
| 5,080,800 A | 1/1992 | Heyl et al. |
| 5,401,811 A | 3/1995 | Stuart, Jr. |
| 5,588,559 A | 12/1996 | Vallet Mas et al. |
| 5,681,463 A | 10/1997 | Shimizu et al. |
| 5,863,562 A | 1/1999 | Tsao et al. |
| 5,936,061 A | 8/1999 | Andersson et al. |
| 6,669,848 B2 | 12/2003 | Kuhn et al. |
| 6,713,646 B2 | 3/2004 | Zhang et al. |
| 6,933,289 B2 | 8/2005 | Lyons et al. |
| 7,622,031 B2 | 11/2009 | Seven et al. |
| 8,658,147 B2 | 2/2014 | Sannino et al. |
| 10,123,904 B2 | 11/2018 | Chauhan et al. |
| 2003/0199507 A1 | 10/2003 | Chang et al. |
| 2006/0093999 A1 | 5/2006 | Hei |
| 2008/0269105 A1 | 10/2008 | Taft et al. |
| 2010/0238447 A1 | 9/2010 | Hirsch |
| 2010/0285192 A1 | 11/2010 | Daoust et al. |
| 2010/0305259 A1 | 12/2010 | Rodriguez et al. |
| 2013/0127071 A1 | 5/2013 | Sugimoto et al. |
| 2015/0374633 A1 | 12/2015 | Fedorchak et al. |
| 2017/0224531 A1 | 8/2017 | Chauhan et al. |
| 2019/0269575 A1 | 9/2019 | Chauhan et al. |
| 2019/0298790 A1 | 10/2019 | Gore et al. |
| 2019/0307641 A1 | 10/2019 | Golub et al. |
| 2020/0246222 A1 | 8/2020 | Malanga et al. |
| 2020/0346186 A1 | 11/2020 | Wilson et al. |

FOREIGN PATENT DOCUMENTS

| | | |
|---|---|---|
| CA | 2537117 A1 | 3/2005 |
| EP | 0745391 A1 | 12/1996 |
| GB | 1087915 A | 10/1967 |
| JP | H08322911 A | 12/1996 |
| WO | WO-2005023665 A1 | 3/2005 |
| WO | WO-2005066219 A1 | 7/2005 |
| WO | WO-2009032266 A2 | 3/2009 |
| WO | WO-2016025560 A1 | 2/2016 |
| WO | WO-2017096203 A1 | 6/2017 |

(Continued)

OTHER PUBLICATIONS

Baudouin, et al. Short term comparative study of topical 2% carteolol with and without benzalkonium chloride in healthy volunteers. Br J Ophthalmol. Jan. 1998; 82(1): 39-42.

Baudouin et al., Preservatives in eyedrops: the good, the bad and the ugly. Progress in Retinal and Eye Research 29: 312-334 (2010).

Clariant International Ltd. Licolub(R) H 12 fine grain. Oxidized, high density polyethylene max. (2014).

Deurex, The Wax Company. Polyethylene waxes, technical data (2020).

(Continued)

*Primary Examiner* — Zohreh A Fay
(74) *Attorney, Agent, or Firm* — Wilson Sonsini Goodrich & Rosati

(57) ABSTRACT

A particulate plug for removing a preservative from a solution, suspension, or emulsion comprising a drug is presented. The plug comprises microparticles of a hydrophobic polymer/fatty acid blend. The microparticles of hydrophobic polymer/fatty acid blend selectively absorb preservative allowing the drug to remain in solution for delivery.

29 Claims, No Drawings

(56) References Cited

FOREIGN PATENT DOCUMENTS

| WO | WO-2018102817 A1 | 6/2018 |
| WO | WO-2019060846 A1 | 3/2019 |

OTHER PUBLICATIONS

International Search Report and Written Opinion dated Nov. 19, 2015 for International PCT Patent Application No. PCT/US2015/044782.

Ishibashi et al., Comparison of the short-term effects on the human corneal surface of topical timolol maleate with and without benzalkonium chloride. Journal of Glaucoma 12(6):486-490 (2003).

Jaenen, et al. Ocular symptoms and signs with preserved and preservative-free glaucoma medications. Eur J Ophthalmol. May-Jun. 2007;17(3):341-9.

Kim et al., Dexamethasone transport and ocular delivery from poly(hydroxyethyl methacrylate) gels. International Journal of Pharmaceutics 353:205-222 (2008).

Nuzzi et al., Conjunctiva and subconjunctival tissue in primary open-angle glaucoma after long-term topical treatment: an immunohistochemical and ultrastructural study. Graefe's Archive for Clinical and Experimental Ophthalmology 233(3):154-162 (1995).

PCT/US2017/064513 International Search Report and Written Opinion mailed Mar. 14, 2018.

PCT/US2018/052477 International Search Report and Written Opinion dated Dec. 20, 2018.

PCT/US2020/016879 International Search Report and Written Opinion dated Apr. 14, 2020.

PCT/US2020/030801 International Search Report and Written Opinion dated Aug. 4, 2020.

Rolando, et al. The Effect of Different Benzalkonium Chloride Concentrations on Human Normal Ocular Surface. The Lacrimal System. Kugler and Ghedini, New York 1991, 87-91.

U.S. Appl. No. 15/502,876 Final Office Action dated May 15, 2018.

U.S. Appl. No. 16/932,623 First Action Interview dated Jan. 4, 2021.

PCT/US2020/066216 International Search Report and Written Opinion dated Mar. 31, 2021.

PRESERVATIVE REMOVAL FROM EYE DROPS

CROSS-REFERENCE

This application is a continuation application of PCT/US2020/066216, filed Dec. 18, 2020, which claims the benefit of U.S. Provisional Application Ser. No. 62/950,866, filed Dec. 19, 2019, each of which is incorporated herein by reference for all purposes.

BACKGROUND

Ophthalmic diseases are commonly treated with prescribed multi-dose medications packaged in eye drop bottles due to ease of use, availability, affordability, and patient compliance. The frequency of topical eye drop application varies from one or two times a day for diseases like glaucoma to as many as ten times a day for severe infections. Although eye drops formulations are packed under sterile conditions, the potential risk of contamination after prolonged use or improper handling can be a key factor contributing to ocular infections. In some cases, as a frugal measure, multiple patients tend to use the same multi-dose containers to administer medications, overlooking the possibility of ocular infections due to cross-contamination, particularly if the protocol for disinfecting the nozzle is not followed. Most ophthalmic formulations now contain an added preservative to maintain the shelf life of the sterile medication and eliminate microbial growth. The United States Food and Drug Administration has imposed regulations on multi-dose ophthalmic formulations, mandating the addition of preservatives to providing microbe-free medication. A variety of preservatives are used to serve this purpose. Preservatives are needed for maintaining sterility, but the benefit is often offset by adverse side effects of the preservatives, even among healthy subjects.

Benzalkonium chloride (BAK), a quaternary ammonium compound with high efficacy, is used prominently. BAK is an active detergent disinfecting agent, which interrupts the lipid membranes of cells, thereby inhibiting the growth of microorganisms. Despite an acceptable tolerance and safety profile of BAK, many studies have shown commercial topical medications with added BAK content to induce severe toxic side effects. Well-documented adverse effects of BAK include tear film instability, trabecular and corneal cells growth retardation and corneal and conjunctival inflammation. Cytotoxicity studies show that BAK disrupts ocular surface cells and tissues, whose impact in glaucoma and dry eye patients requiring long-term and frequent dosing is deleterious. Corneal endothelial damage occurs upon prolonged use of topical medication with added benzalkonium chloride. High tear film instability and disruption of the corneal barrier is observed using the preserved glaucoma drug Timolol to a greater extent than when using preservative-free Timolol in healthy subjects. The detergent action of BAK solution disrupts superficial lipid layers of the tear film into oil droplets solubilized by a single drop of 0.01% BAK solution.

SUMMARY

Embodiments of the disclosure are directed to particulate plugs comprising hydrophobic polymer/fatty acid blend comprising a hydrophobic polymer and a fatty acid in a ratio from about 1:1 to about 1:20 for selectively removing a large fraction of the preservative without significantly removing the drug and specifically directed to achieving this for each eluting drop. The material of the plug may be designed to minimize drug binding. The material of the plug may depend on the properties of the drug whose binding is to be minimized. The binding may depend on the structure of the drug and/or the detailed structure of the matrix materials of the particles of the tip. Broadly, ophthalmic drugs can be divided into hydrophobic and hydrophilic categories depending of the affinity of the drug for water. Hydrophilic drugs are more soluble in water while hydrophobic drugs are less soluble.

Embodiments of the disclosure are directed to particulate plugs for removing a preservative from a drug solution where microparticles comprising the plug are hydrophobic polymer/fatty acid blend comprising a hydrophobic polymer and a fatty acid in a ratio from about 1:1 to about 1:20.

The drug can be a hydrophilic drug selected from Tables 1-4 such as, for example, Timolol Maleate, Levofloxacin, Dorzolamide, Brimonidine Tartrate, and/or hydrophobic drugs, for example, latanoprost or bimatoprost, and/or a combination of drugs, for example, Combigan. The preservative may be Benzalkonium chloride (BAK).

One embodiment provides a particulate plug for removing a preservative from a solution, suspension, or emulsion comprising a drug, the particulate plug comprising microparticles of a hydrophobic polymer/fatty acid blend, wherein the microparticles form a particulate plug capable of being fitted to an outlet of a container for the solution, emulsion, or suspension, wherein the particulate plug rapidly and selectively removes a preservative from the solution, emulsion, or suspension.

Another embodiment provides the particulate plug wherein the microparticles have a dimension of 5 µM to about 10,000 µM.

Another embodiment provides the particulate plug wherein the preservative comprises benzalkonium chloride (BAK).

Another embodiment provides the particulate plug wherein the drug is selected from Table 1, Table 2, Table 3, or Table 4.

Another embodiment provides the particulate plug wherein the hydrophobic polymer/fatty acid blend comprises a hydrophobic polymer selected from isotactic polypropylene, low density polyethylene, or high density polyethylene. Another embodiment provides the particulate plug wherein the isotactic polypropylene has an average MW of about 250,000. Another embodiment provides the particulate plug wherein the hydrophobic polymer/fatty acid blend comprises a hydrophobic polymer that is a thermoplastic. Another embodiment provides the particulate plug wherein the hydrophobic polymer/fatty acid blend comprises a hydrophobic polymer that is a thermoset. Another embodiment provides the particulate plug wherein the hydrophobic polymer/fatty acid blend comprises a product of a melt blend. Another embodiment provides the particulate plug wherein the hydrophobic polymer/fatty acid blend comprises a product of a solution blend. Another embodiment provides the particulate plug wherein the hydrophobic polymer/fatty acid blend comprises a product of a spray-dry blend.

Another embodiment provides the particulate plug wherein the hydrophobic polymer/fatty acid blend comprises a fatty acid selected from a fatty acid having the structure of $CH_3(CH_2)_nCO_2H$, wherein n is 2 to 24. Another embodiment provides the particulate plug wherein n is 6 to 24. Another embodiment provides the particulate plug wherein n is 8 to 24. Another embodiment provides the particulate plug wherein n is 8 to 20. Another embodiment provides the particulate plug wherein n is 10 to 20. Another embodiment provides the particulate plug wherein n is 12 to 20. Another embodiment provides the particulate plug wherein n is 14 to 20. Another embodiment provides the particulate plug wherein n is 14 to 18. Another embodiment provides the particulate plug wherein n is 14 or 16. Another embodiment provides the particulate plug wherein n is 16. Another embodiment provides the particulate plug wherein the fatty acid is selected from caprylic acid, capric acid, lauric acid, myristic acid, palmitic acid, stearic acid, arachidic acid, behenic acid, lignoceric acid, or cerotic acid. Another embodiment provides the particulate plug wherein the fatty acid is selected from Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, or Docosahexaenoic acid. Another embodiment provides the particulate plug wherein the fatty acid is selected from a fatty acid having a melting point greater than 70° C.

Another embodiment provides the particulate plug wherein the weight-to-weight ratio of the hydrophobic polymer-to-fatty acid is from about 1:1 to about 1:20. Another embodiment provides the particulate plug wherein the weight-to-weight ratio of the hydrophobic polymer-to-fatty acid is about 1:1. Another embodiment provides the particulate plug wherein the weight-to-weight ratio of the hydrophobic polymer-to-fatty acid is about 1:2. Another embodiment provides the particulate plug wherein the weight-to-weight ratio of the hydrophobic polymer-to-fatty acid is about 1:3. Another embodiment provides the particulate plug wherein the weight-to-weight ratio of the hydrophobic polymer-to-fatty acid is about 1:4. Another embodiment provides the particulate plug wherein the weight-to-weight ratio of the hydrophobic polymer-to-fatty acid is about 1:5. Another embodiment provides the particulate plug wherein the weight-to-weight ratio of the hydrophobic polymer-to-fatty acid is about 1:6. Another embodiment provides the particulate plug wherein the weight-to-weight ratio of the hydrophobic polymer-to-fatty acid is about 1:7. Another embodiment provides the particulate plug wherein the weight-to-weight ratio of the hydrophobic polymer-to-fatty acid is about 1:8. Another embodiment provides the particulate plug wherein the weight-to-weight ratio of the hydrophobic polymer-to-fatty acid is about 1:9. Another embodiment provides the particulate plug wherein the weight-to-weight ratio of the hydrophobic polymer-to-fatty acid is about 1:10.

Another embodiment provides the particulate plug wherein the microparticles have a dimension of 5 μM to about 50 μM. Another embodiment provides the particulate plug wherein the microparticles have a dimension of 50 μM to about 100 μM. Another embodiment provides the particulate plug wherein the microparticles have a dimension of 100 μM to about 500 μM. Another embodiment provides the particulate plug wherein the microparticles have a dimension of 500 μM to about 1000 μM. Another embodiment provides the particulate plug wherein the microparticles have a dimension of 1,000 μM to about 10,000 μM.

One embodiment provides a hydrophobic polymer/fatty acid blend comprising a hydrophobic polymer and a fatty acid in a ratio from about 1:1 to about 1:20. Another embodiment provides the blend wherein the hydrophobic polymer and the fatty are combined in a vessel suitable for chemical reaction; heated to above the melting point of each component forming a homogenous composition; and poured into cool water.

One embodiment provides a particulate plug, for removing a preservative from a solution, suspension, or emulsion comprising a drug, the particulate plug comprising microparticles of a hydrophobic polymer/fatty acid blend, wherein the microparticles form a particulate plug capable of being fitted to an outlet of a container for the solution, emulsion, or suspension, wherein the particulate plug rapidly and selectively removes a preservative from the solution, emulsion, or suspension, wherein the hydrophobic polymer/fatty acid blend comprises a hydrophobic polymer and a fatty acid in a ratio from about 1:1 to about 1:20. Another embodiment provides the particulate plug wherein the blend is prepared by the process of the hydrophobic polymer and the fatty are combined in a vessel suitable for chemical reaction; heated to above the melting point of each component forming a homogenous composition; and poured into cool water.

One embodiment provides a particulate plug for removing a preservative from a solution, suspension, or emulsion comprising a drug, the particulate plug comprising microparticles of a fatty acid, wherein the microparticles form a particulate plug capable of being fitted an outlet of a container for the solution, emulsion, or suspension, wherein the particulate plug rapidly and selectively removes a preservative from the solution, emulsion, or suspension. Another embodiment provides the particulate plug wherein the fatty acid is stearic acid.

One embodiment provides a particulate plug for removing a preservative from a solution, suspension, or emulsion comprising a drug, the particulate plug consisting essentially of microparticles of a fatty acid, wherein the microparticles form a particulate plug capable of being fitted an outlet of a container for the solution, emulsion, or suspension, wherein the particulate plug rapidly and selectively removes a preservative from the solution, emulsion, or suspension. Another embodiment provides the particulate plug wherein the fatty acid is stearic acid.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DETAILED DESCRIPTION

The present disclosure provides a preservative removal agent. A preservative removal agent may rapidly and selectively remove preservatives of the present disclosure from a solution, emulsion, or suspension comprising a therapeutic agent. The preservative removal agent may rapidly and selectively extract the preservative, allowing the eye drop formulation to flow through the plug with minimal pressure drop, yet with sufficient time to remove the preservative and with sufficient surface area to adsorb the preservative. The matrix may comprise a material with a high affinity for the preservative, such as for example benzalkonium chloride (BAK), and low affinity for a therapeutic agent, such as a drug or other ophthalmological agent.

In 2009, the European Medicines Agency's Committee for Medicinal Products for Human Use concluded that unpreserved formulations "are needed for patients with lower tolerance to preservatives," and "for long-term treatment, formulations without preservatives are valuable alternatives." Considering the adverse effects of preservatives, the development of safe eye drop dispensing devices to deliver preservative-free formulations has been pursued for more than a decade. Preservative-free formulations are available in single-dose containers to eliminate the need for preservatives; however, these are not convenient and too expensive for wide public use.

It would therefore be useful to have systems and methods for delivering a preservative free ophthalmic drug to the eye, whereby a preserved ophthalmic solution is dispensed through a media at the tip that accomplishes one or more of the following:

i. Would effectively remove all the preservative (e.g., benzalkonium chloride);
ii. Would have a high BAK uptake (partition coefficient);
iii. Would leave the API largely (nearly 100%) unreduced or unhindered or unabsorbed;
iv. Would consist of ridged, flowing particles, mostly free of fine particulate matter;
v. Would have low restriction of liquid flow;
vi. Would allow for higher viscosity drug formulations to be used; and
vii. Was largely unaffected by the pH of the drug formulation in accomplishing the above.

Preservative Removal Agent

In some embodiments, the disclosure provides pharmaceutical formulations comprising a preservative and a therapeutic agent. The formulation may comprise a solution, emulsion, or suspension of a therapeutic agent and a preservative. In some embodiments, the formulation may comprise a preservative removal agent, (e.g., in embodiments where the preservative removal agent may comprise a portion of a solution, emulsion, or suspension comprising a therapeutic agent and a preservative). In other embodiments, the preservative removal agent may be separate from the solution, emulsion, or suspension comprising the therapeutic agent and the preservative (e.g., in embodiments where the preservative removal agent may be located within the neck of a bottle). Optionally in any embodiment, the solution, emulsion, or suspension may additionally comprise one or more pharmaceutically acceptable excipients.

A preservative removing device may comprise a matrix. In some embodiments, a matrix may be a particulate plug. In some embodiments, a matrix disposed within a nozzle may be a porous polymeric matrix. Applying a pressure behind the nozzle may cause fluid to flow through the nozzle via the flow path, along which path the preservative may be removed by adsorption onto the matrix. The polymer material, the hydraulic permeability, the partition coefficient, the adsorption rate, and the pore size in combination may provide for the absorption of all or most of the preservative from the solution and thus from the drop administered to the patient eye. The reduced-preservative solution may subsequently be delivered directly to the eye. The porous polymeric matrix may rapidly and selectively extract the preservative, allowing the eye drop formulation to flow through the plug with minimal pressure drop, yet with sufficient time to remove the preservative and with sufficient surface area to adsorb the preservative.

The matrix (e.g., particulate plug) may comprise a blend of a hydrophobic polymer and a fatty acid in a ratio from about 1:1 to about 1:20. Such material may be safe and biocompatible. The matrix comprises a material with a high affinity for the preservative, such as for example benzalkonium chloride (BAK), and low affinity for a drug or other ophthalmological agent. The porous hydrophobic polymer/fatty acid blend may comprise a high affinity for the preservative, such that at least 50 percent of the preservative may be removed and at least 50 percent of the drug may be retained by the solution. In some embodiments, a matrix disposed within a nozzle may be a porous polymeric matrix.

The polymer/fatty acid blend may comprise a weight-to-weight percentage of fatty acid which is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. The polymer/fatty acid blend may comprise a weight-to-weight percentage of fatty acid which is no greater than 5%, no greater than 10%, no greater than 15%, no greater than 20%, no greater than 25%, no greater than 30%, no greater than 35%, no greater than 40%, no greater than 45%, no greater than 50%, no greater than 55%, no greater than 60%, no greater than 65%, no greater than 70%, no greater than 75%, no greater than 80%, no greater than 85%, no greater than 90%, no greater than 95%, or no greater than 99%. Examples of ranges which the weight-to-weight percentage fatty acid falls within can be created by combining any two of the preceding percentages. For example, the polymer/fatty acid blend may comprise a weight-to-weight percentage of fatty acid which is from 5% to 99%, by 10% to 95%, by 20% to 70% or by 35% to 55%.

The polymer/fatty acid blend may comprise a weight-to-weight percentage of hydrophobic polymer which is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. The polymer/fatty acid blend may comprise a weight-to-weight percentage of hydrophobic polymer which is no greater than 5%, no greater than 10%, no greater than 15%, no greater than 20%, no greater than 25%, no greater than 30%, no greater than 35%, no greater than 40%, no greater than 45%, no greater than 50%, no greater than 55%, no greater than 60%, no greater than 65%, no greater than 70%, no greater than 75%, no greater than 80%, no greater than 85%, no greater than 90%, no greater than 95%, or no greater than 99%. Examples of ranges which the weight-to-weight percentage hydrophobic polymer falls within can be created by combining any two of the preceding percentages. For example, the polymer/fatty acid blend may comprise a weight-to-weight percentage of hydrophobic polymer which is from 5% to 99%, by 10% to 95%, by 20% to 70% or by 35% to 55%.

The weight-to-weight ratio of a fatty acid to a polymer (e.g., a hydrophobic polymer) can be about 100:about 1, about 95:about 1, about 90:about 1, about 85:about 1, about 80:about 1, about 75:about 1, about 70:about 1, about 65:about 1, about 60:about 1, about 55:about 1, about 50:about 1, about 45:about 1, about 40:about 1, about 35:about 1 about 30:about 1, about 25:about 1, about 20:about 1, about 15:about 1, about 10:about 1, about 9:about 1, about 8:about 1, about 7:about 1, about 6:about 1, about 5:about 1, about 4:about 1, about 3:about 1, about 2:about 1, about 1:about 1, about 1:about 2, about 1:about 3, about 1:about 4, about 1:about 5, about 1:about 6, about 1:about 7, about 1:about 8, about 1:about 9, or about 1:about 10. The weight-to-weight ratio of a fatty acid to a polymer (e.g., a hydrophobic polymer) can be within the range of between about 100:about 1 and about 1 to about 10, between about 10:about 1 and about 1:about 1, between about 5:about 1 and about 2:about 1.

The matrix material (e.g., particulate plug) may comprise a blend of a fatty acid and a polymer. The matrix may comprise a blend of a hydrophobic polymer and a fatty acid. The matrix may comprise a blend of a polypropylene and a fatty acid. The matrix may comprise a blend of a polypropylene and steric acid. The polymer/fatty acid blend may comprise a hydrophobic polymer selected from isotactic polypropylene, low density polyethylene, or high density polyethylene.

The matrix materials disclosed herein are not limited to fatty acids blended with homopolymers and copolymers of polypropylene. The matrix materials disclosed herein may also comprise fatty acids blended with other types of homopolymeric or copolymeric crystallizable or partially crystallizable poly-alpha-olefins, such as, homopolymers and copolymers of ethylene, propylene, 1-butene, 4-methyl-1-pentene, 3-methyl-1-butene, 4,4-dimethyl-1-pentene, 3-methyl-1-pentene, 4-methyl-1-hexene, 5-ethyl-1-hexene, 6-methyl-1-heptene, 1-hexene, 1-heptene, 1-octene, 1-nonene, 1-decene, and the like. Also included are oxidized waxes formed by the Fischer-Tropsch process.

The polymer of the polymer/fatty acid blend may be a hydrophobic polymer. Hydrophobic polymers may be generally water repellant. Hydrophobic polymers may generally not be soluble in water. Hydrophobic polymers may comprise homopolymers or copolymers of materials such as polyethylene, polystyrene, polyvinylchloride, polytetrafluorethylene, polydimethylsiloxane, some polyesters, some polyurethanes, acrylics, epoxies, etc. The hydrophobic polymer/fatty acid blend may comprise a hydrophobic polymer selected from isotactic polypropylene, low density polyethylene, or high density polyethylene.

A polypropylene may comprise a crystallinity. Polypropylene may be characterized as isotactic, syndiotactic, or atactic. The term tacticity may describe how the methyl group is oriented in the polymer chain of polypropylene. Tacticity may be indicated in percent, using the isotactic index (according to DIN 16774). Isotactic polypropylene may comprise methyl groups which are substantially located at the same side. Isotactic polypropylene may be helical in shape. An isotactic propylene may comprise a semi-crystalline structure. The higher the isotacticity (e.g., the isotactic fraction), the greater the crystallinity, which may result in a higher softening point, rigidity, elastic-modulus, and hardness. Atactic polypropylene may lack regularity of the orientation of the methyl groups in the chain. Atactic polypropylene may be less crystalline and more amorphous. Syndiotactic polypropylene may comprise methyl groups which are substantially alternating.

An isotactic polypropylene may comprise a tacticity between 85% and 95%, between 85% and 99%, between 90% and 100%, etc. An isotactic polypropylene may comprise a tacticity greater than 85%, greater than 90%, greater than 95%, greater than 99% or more. Syndiotactic polypropylene may comprise methyl groups which are substantially alternating. Syndiotactic polypropylene may comprise greater than 85% racemo diads, greater than 90% racemo diads, greater than 95% racemo diads, greater than 99% racemo diads, or more. Atactic polypropylene may comprise less than 99% meso diads, less than 98% meso diads, less than 95% meso diads, less than 90% meso diads, less than 85% meso diads, or less.

Isotactic polypropylene may exist in several crystal structures. The crystalline modifications may be categorized as having $\alpha$-, $\beta$- and $\gamma$-modification as well as mesomorphic (smectic) forms. The $\alpha$-modification may be common in isotactic polypropylene. Crystals with $\alpha$-modifications may comprise lamellae in the form of folded chains. The lamellae may be arranged a "cross-hatched" structure. The melting point of $\alpha$-crystalline regions may be 185 to 220° C. The density may be 0.936 to 0.946 g·cm-3. The $\beta$-modification may be somewhat less ordered. The $\beta$-modification may be formed faster. The $\beta$-modification may have a lower melting point of 170 to 200° C. The formation of the $\beta$-modification may be promoted by nucleating agents, suitable temperatures, and shear stress. The mesomorphic form may result from quick cooling of the polypropylene. The degree of order of the mesomorphic phase may range between the crystalline and the amorphous phase. The density of the mesomorphic phase may comprise a density of about 0.916 g·cm-3.

The length of a polypropylene (e.g., isotactic polypropylene) may be characterized by a molecular weight. The molecular weight may be about 250,000 g/mol. The molecular weight may be greater than about 10,000, about 20,000, about 50,000, about 100,000, about 200,000, about 210,000, about 220,000, about 230,000, about 240,000, about 250,000, about 260,000, about 270,000, about 280,000, about 290,000, about 300,000, about 300,000, or more.

Polypropylene may be characterized by a melting point. The melting point of polypropylene may occur in a range, so the melting point may be determined by finding the highest temperature of a differential scanning calorimetry chart. High tacticity, isotactic polypropylene may have a melting point of about 171° C. (340° F.). Lower tacticity isotactic polypropylene may have a melting point that ranges from 160 to 166° C. (320 to 331° F.), depending on atactic material and crystallinity. Syndiotactic polypropylene with a crystallinity of 30% may have a melting point of 130° C. (266° F.).

In some cases, the polymer of the polymer/fatty acid blend (e.g., hydrophobic polymer/fatty acid blend) may be characterized by a melting point. The melting point of a polymer of the polymer/fatty acid blend may be greater than 70° C. The melting point of a polymer of a polymer/fatty acid blend may be greater than 40° C., 50° C., 60° C., 70° C., 80° C., 90° C., 100° C., 110° C., 120° C., 130° C., 140° C., 150° C., 160° C., 170° C., 180° C., 190° C., 200° C., 300° C., 400° C., 500° C., 600° C., 700° C., 800° C., 900° C., 1000° C., or more. The melting point of a polymer of a polymer/fatty acid blend may be less than 1000° C., 900° C., 800° C., 700° C., 600° C., 500° C., 400° C., 300° C., 200° C., 100° C., or less. The melting point of a polymer of a polymer/fatty acid blend may be within a range defined by any two of the preceding values.

The matrix material (e.g., particulate plug) may comprise a blend of a fatty acid and a polymer. The matrix may comprise a blend of a polymer and a saturated fatty acid. The matrix may comprise a blend of a polymer and steric acid. The matrix may comprise a blend of a polypropylene and steric acid.

In some embodiments, a fatty acid may comprise a saturated, monounsaturated, or polyunsaturated fatty acid. A saturated fatty acid may not comprise C=C double bonds. An unsaturated fatty acid may comprise one or more C=C double bonds. A fatty acid may comprise any of the saturated, monounsaturated, or polyunsaturated fatty acid disclosed herein.

A saturated fatty acid may be characterized by a number of carbon atoms, e.g., C3 where three is the number of carbon atoms. In some embodiments, a saturated fatty acid is a C2-C28 fatty acid. In some embodiments, a saturated fatty acid is a C10-C25 fatty acid. In some embodiments, a saturated fatty acid is a C16-C20 fatty acid. In some embodiments, a saturated fatty acid is a greater than C10 fatty acid. In some embodiments, a saturated fatty acid is a greater than C14 fatty acid.

A saturated fatty acid may comprise one or more of: Propanoic acid, Butanoic acid, Pentanoic acid, Hexanoic acid, Heptanoic acid, Octanoic acid, Nonanoic acid, Decanoic acid, Undecanoic acid, Dodecanoic acid, Tridecanoic acid, Tetradecanoic acid, Pentadecanoic acid, Hexadecanoic acid, Heptadecanoic acid, Octadecanoic acid, Nonadecanoic acid, Eicosanoic acid, Heneicosanoic acid, Docosanoic acid, Tricosanoic acid, Tetracosanoic acid, Pentacosanoic acid, Hexacosanoic acid, Heptacosanoic acid, Octacosanoic acid, Nonacosanoic acid, Triacontanoic acid, Hentriacontanoic acid, Dotriacontanoic acid, Tritriacontanoic acid, Tetratriacontanoic acid, Pentatriacontanoic acid, Hexatriacontanoic acid, Heptatriacontanoic acid, Octatriacontanoic acid, Nonatriacontanoic acid, or Tetracontanoic acid.

An unsaturated fatty acid may generally be referred to by the following conventions. The carbon next to the carboxylate is known as a, the next carbon β, and so forth. Since biological fatty acids can be of different lengths, the last position is labelled as a "ω", the last letter in the Greek alphabet. The physiological properties of unsaturated fatty acids may correlate with the position of the first unsaturation relative to the end position (ω). For example, the term ω-3 signifies that the first double bond exists as the third carbon-carbon bond from the terminal end (ω) of the carbon chain. The number of carbons and the number of double bonds may also be listed in short descriptions of unsaturated fatty acids. For instance, ω-3 C18:4, or C18:4 ω-3, or C18:4 n-3 indicates stearidonic acid, an 18-carbon chain with 4 double bonds, and with the first double bond in the third position from the $CH_3$ end.

A blend may comprise a monounsaturated fatty acid. A monounsaturated fatty acid may comprise one or more of Crotonic acid, Myristoleic, Palmitoleic acid, Sapienic acid, Oleic acid, Elaidic acid, Vaccenic acid, Gadoleic acid, Eicosenoic acid, Erucic acid, or Nervonic acid.

A monounsaturated fatty acid may be characterized by a number of carbon atoms, e.g., C3:1 where three is the number of carbon atoms and 1 is the number of double bonds. In some embodiments, a monounsaturated fatty acid is a C2:1-C28:1 fatty acid. In some embodiments, a monounsaturated fatty acid is a C10:1-C25:1 fatty acid. In some embodiments, a monounsaturated fatty acid is a C16:1-C20:1 fatty acid. In some embodiments, a monounsaturated fatty acid is a greater than C10:1 fatty acid. In some embodiments, a monounsaturated fatty acid is a greater than C14:1 fatty acid.

A blend may comprise a polyunsaturated fatty acid. A polyunsaturated fatty acid may comprise one or more of: Linoleic acid, Eicosadienoic acid, Docosadienoic acid, Linolenic acid, Pinolenic acid, Eleostearic acid, Mead acid, Dihomo-γ-linolenic acid, Eicosatrienoic acid, Stearidonic acid, Arachidonic acid, Eicosatetraenoic acid, Adrenic acid, Bosseopentaenoic acid, Eicosapentaenoic acid, Ozubondo acid, Sardine acid, Tetracosanolpentaenoic acid, Cervonic acid, and Herring acid.

A polyunsaturated fatty acid may be characterized by a number of carbon atoms, e.g., C3:1 where three is the number of carbon atoms and 1 is the number of double bonds. In some embodiments, a di-unsaturated fatty acid is a C2:2-C28:2 fatty acid. In some embodiments, a di-unsaturated fatty acid is a C10:2-C25:2 fatty acid. In some embodiments, a di-unsaturated fatty acid is a C16:2-C20:2 fatty acid. In some embodiments, a di-unsaturated fatty acid is a greater than C10:2 fatty acid. In some embodiments, a di-unsaturated fatty acid is a greater than C14:2 fatty acid.

In some embodiments, a polyunsaturated fatty acid is a CM:N ω-L fatty acid, where N and L are numbers of less than M. In some embodiments, a poly-unsaturated fatty acid is a C10:N—C25:N ω-L fatty acid. In some embodiments, a poly-unsaturated fatty acid is a C16:N—C20:N ω-L fatty acid. In some embodiments, a poly-unsaturated fatty acid is a greater than C10:N ω-L fatty acid. In some embodiments, a poly-unsaturated fatty acid is a greater than C14:N ω-L fatty acid.

In some embodiments a fatty acid may include caprylic acid, capric acid, lauric acid, myristic acid, palmitic acid, stearic acid, arachidic acid, behenic acid, lignoceric acid, or cerotic acid Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, Docosahexaenoic acid, or the like.

In some cases, the fatty acid of the polymer/fatty acid blend (e.g., hydrophobic polymer/fatty acid blend) may be characterized by a melting point. The melting point of a fatty acid of a polymer/fatty acid blend may be greater than 70° C. The melting point of a fatty acid of a polymer/fatty acid blend may be greater than 40° C., 50° C., 60° C., 70° C., 80° C., 90° C., 100° C., 110° C., 120° C., 130° C., 140° C., 150° C., 160° C., 170° C., 180° C., 190° C., 200° C., 300° C., 400° C., 500° C., 600° C., 700° C., 800° C., 900° C., 1000° C., or more. The melting point of a fatty acid of a polymer/fatty acid blend may be less than 1000° C., 900° C., 800° C., 700° C., 600° C., 500° C., 400° C., 300° C., 200° C., 100° C., or less. The melting point of a fatty acid of a polymer/fatty acid blend may be within a range defined by any two of the preceding values.

The present disclosure provides methods of manufacturing a particulate plug comprising a polymer/fatty acid blend. A polymer/fatty acid blend may be formed by combining powders of the polymer and the fatty acid to be blended. Heating the mixture to a melt and, optionally, stirring. The resultant material may be added to water. The wet cooled material may be dried, e.g., vacuum dried. The dried blended material may be added to a grinder and ground until a particle size is reached. The resultant particles may be packed to form a particulate plug. The plug may be disposed proximate an outlet of a container, such as a compressible bottle (e.g., an eyedrop bottle).

Methods of manufacturing a particulate plug comprising a polymer/fatty acid blend may also include solution blending or spray dry blending. For example, each of the polymer and the fatty acid may be dissolved, the resultant solutions may be mixed, and the solvent may be removed, for example, by decanting of off a precipitate, evaporation, etc.

In certain embodiments, particles (e.g., microparticles) described herein have an average largest dimension from about 1 nm to about 10 μm, about 1 nm to about 5 μm, about 1 nm to about 2 μm, about 1 nm to about 1 μm, about 1 nm to about 900 nm, about 1 nm to about 800 nm, about 1 nm to about 700, about 1 nm to about 600 nm, about 1 nm to about 500 nm, about 1 nm to about 400 nm, about 1 nm to about 300 nm, about 1 nm to about 200 nm, or even from about 1 nm to about 100 nm. In certain embodiments, the average largest dimension is the average largest diameter or the average equivalent diameter.

In certain embodiments, greater than 80%, greater than 90% or greater than 95% of the particles (e.g., microparticles) have an average largest particle diameter of from about 1 nm to about 10 µm, about 1 nm to about 5 µm, about 1 nm to about 2 µm, about 1 nm to about 1 µm, about 1 nm to about 900 nm, about 1 nm to about 800 nm, about 1 nm to about 700 nm, about 1 nm to about 600 nm, about 1 nm to about 500 nm, about 1 nm to about 400 nm, about 1 nm to about 300 nm, about 1 nm to about 200 nm, or even from about 1 nm to about 100 nm. In certain embodiments, the average diameter is the average largest diameter or the average equivalent diameter.

In certain embodiments, particles (e.g., microparticles) described herein have an average diameter from about 100 nm to about 10 µm, about 100 nm to about 5 µm, about 100 nm to about 2 µm, about 100 nm to about 1 µm, about 100 nm to about 900 nm, about 100 nm to about 800 nm, about 100 nm to about 700 nm, about 100 nm to about 600 nm, about 200 nm to about 500 nm, about 250 nm to about 600 nm, about 300 nm to about 600 nm, about 350 nm to about 700 nm, about 450 nm to about 550 nm, about 475 nm to about 525 nm, or from about 400 nm to about 700 nm. In certain embodiments, the average diameter is the average largest diameter or the average equivalent diameter.

In certain embodiments, greater than 80%, greater than 90% or greater than 95% of the particles (e.g., microparticles) have an average diameter from about 100 nm to about 10 µm, about 100 nm to about 5 µm, about 100 nm to about 2 µm, about 100 nm to about 1 µm, about 100 nm to about 900 nm, about 100 nm to about 800 nm, about 100 nm to about 700 nm, about 100 nm to about 600 nm, about 200 nm to about 500 nm, about 250 nm to about 600 nm, about 300 nm to about 600 nm, about 350 nm to about 700 nm, about 450 nm to about 550 nm, about 475 nm to about 525 nm, or from about 400 nm to about 700 nm. In certain embodiments, the average diameter is the average largest diameter or the average equivalent diameter.

In some cases, the drug's (e.g., ophthalmic agent's) partition coefficient into the matrix may be lower by at least an order of magnitude than the matrix's affinity for the preservative. For example, the particulate plug may bind BAK with a partition coefficient of about 100-500 depending on the BAK concentration and the structure of the particulate plug. In some embodiments, the particulate plug may comprise a partition coefficient for the preservative from the solution, emulsion, or suspension of, for example, at least 10, at least 100, at least 1000, at least 10,000, or within a range defined by any two of the preceding values. Additionally, or alternatively, the adsorption rate constant may be sufficiently high so that the time for adsorption of a drug molecule to the polymer may be less than the time to form a drop. The time to form a drop may comprise a time within a range from 0.1 to 10 seconds. The time to form a drop may be about 2 seconds, between about 1 second and 5 seconds, about 3 seconds, less than 5 seconds, etc.

The uptake of the drug or therapeutic agent by the particulate plug may be characterized by a percent uptake. The percent uptake may be expressed as percentage of the original drug concentration which is delivered after passing through the particulate plug. In some cases, the percent uptake may be less than 20%, less than 10%, less than 5%, less than 2%, less than 1%, or less. In some cases, the percent uptake may be about 2%. In some cases, the percent uptake may be about 1%.

The uptake of the preservative by the particulate plug may be characterized by a percent uptake. The percent uptake may be expressed as percentage of the original preservative concentration which is delivered after passing through the particulate plug. In some cases, the percent uptake may be greater than 80%, greater than 90%, greater than 95%, greater than 98%, greater than 99%, or more. In some cases, the percent uptake may be about 98%. In some cases, the percent uptake may be about 99%. In some cases, the preservative may be undetectable after passing though the particulate plug. In some cases, the preservative may be below a detectable threshold based on comparison of the area counts of the HPLC peaks of the starting solution to the area counts of the drop, etc. In some cases, the preservative may be below a detectable threshold based on UV absorption.

The matrix (e.g., the particulate plug) may display a high hydraulic permeability such that relatively little pressure may be required to dispense a fluid. The hydraulic permeability may depend on the matrix material, its dimensions, and how it is packed. Larger pores or channels around packed particles or within the particles themselves may allow for higher flow for a given pressure drop. In some embodiments, hydraulic permeability may be larger than about 0.01 Darcy. A nozzle may comprise a permeability of about 0.1 Darcy. A hydraulic permeability of 1 to 10 Darcy may allow fluid to be retained in the filter during instances when the pressure may be lowered subsequent to formation of a drop. A larger hydraulic permeability may allow the same plug to work for a wide range of formulations including, for example, high viscosity formulations, such as rewetting eye drops. In some embodiments, the porous polymeric matrix comprises a hydraulic permeability of, for example, 0.01 Da, 0.1 Da, 1 Da, 10 Da, 100 Da, 1000 Da or a hydraulic permeability within a range defined by any two of the preceding values.

In some embodiments, the matrix may be highly porous containing large channels through which liquid can flow. The pore or channel size in the matrix may be small enough so that the molecules, which may initially be far from the surface of the polymer in the matrix, may diffuse towards the polymer and adsorb. A matrix may comprise large interconnected pores or channels which may allow flow of solution and adsorption of the preservative into the pores or channels. The matrix may be formed as a porous gel, as a packed bed, and/or a structure formed by 3D printing soft lithography, electrospinning, or any other appropriate method. In some embodiments, the matrix may comprise a microporous gel. In some embodiments, the matrix comprises a packed bed of hydrophobic polymer/fatty acid blend particles. The particles may be macroporous.

In some embodiments, the particles may need to be stably held in the nozzle from which the formulation elutes from a container and thereby prevented from eluting from the nozzle. In some cases, the matrix may be sintered to fuse the particulate plug into porous monolith. In some cases, the device may have a cartridge or other assembly to retain the matrix in the nozzle. The device may have a solution permeable bag to retain the matrix. The device may comprise solid walls with a solution permeable bottom. The device may comprise entrance and exit faces with a matrix material therebetween. The entrance and exit faces may comprise solution permeable membranes. The entry and exit faces may comprise a filter. The entrance and exit faces may comprise a screen. The particles may be attached to the container walls through long polymeric chains and/or by placing a filter at the exit from the device. The device may comprise a packaging for delivery to a patient. The packaging may secure the device such that the device may not be compressed until the device is delivered to the patient. The packaging may secure the exit face from allowing the formulation to exit the bottle. The packaging may comprise a removable cap, a break-off cap, a resealable cap, etc.

The matrix may comprise a tortuosity such that the flow path of a solution, emulsion, or suspension through the nozzle may be significantly increased. In an embodiment where the matrix is a packed bed of macroporous particles, the packed beds of macroporous particles may have three levels of porosity: the space between the particles, the macropores in the particles, and the inherent porosity of the polymer. In some embodiments, all three levels of porosity may contribute to the tortuosity of the matrix.

Therapeutic Agent

Embodiments of the present disclosure may provide a therapeutic agent for delivery to an eye selected from a therapeutic agent listed in Tables 1-4. A therapeutic agent may be integrated into a fluid, which may flow from a container to an eye through a nozzle comprising a matrix comprising a polymer/fatty acid blend. In some embodiments, the fluid may comprise a solution, emulsion, or suspension comprising a therapeutic agent. The solution, emulsion, or suspension may comprise a therapeutic agent.

Example therapeutic agents which may be used in conjunction with a nozzle include but are not limited to: timolol, dorzolamide, dexamethasone phosphate, dexamethasone, Betimol®, olopatadine, brimonidine, tetrahydrozoline, latanoprostene bunod, latanoprost, and combinations of any two or more thereof. Therapeutic agents may comprise brand name drugs and formulations including, but not limited to, Timoptic, Xalatan, Combigan, Lumigan, Pataday, Pazeo, Trusopt, Cosopt, Alphagan, Visine, Vyzulta, Veseneo, and other agents described herein such as in the following tables. The therapeutic agents may be dissolved in aqueous solution. The solution may be sterilized and buffered to appropriate pH. In some embodiments, the solution may comprise inactive ingredients such as sodium chloride, sodium citrate, hydroxyethyl cellulose, sodium phosphate, citric acid, sodium dihydrogen phosphate, polyoxyl 40 hydrogenated castor oil, tromethamine, boric acid, mannitol, edetate disodium, sodium hydroxide, and/or hydrochloric acid.

In some embodiments, the fluid comprises a preservative in addition to a therapeutic agent. Example preservatives include but are not limited to: benzalkonium chloride (BAK), alcohols, parabens, methyl paraben, propylparaben, EDTA, chlorhexidine, quaternary ammonium compounds, Purite®, stabilized oxychloro complexes, Sofzia®, sorbic acid, Sodium perborate, polyquaternium-1, chlorobutanol, cetrimonium chloride, edatate disodium, etc. In some embodiments, the preservative is benzalkonium chloride (BAK). In some embodiments, the preservative is one or more quaternary ammonium compounds. In some embodiments, the preservative is polyquaternium-1. In some embodiments, the preservative is cetrimonium chloride.

Therapeutic agents for the treatment of for example, dry eye, bacterial infection, glaucoma, hypertension, inflammation, allergic conjunctivitis, hypotrichosis of the eyelashes, fungal infection, etc. and therapeutic agents used for local anesthetic, pupil dilation, etc. may be administered to a patient as a solution, emulsion, or suspension delivered to an eye topically via a dropper bottle or similar delivery mechanism. The solution, emulsion, or suspension may be subject to contamination such as microbial, fungal, or particulate contamination, which may be averse to patient health. In order to prevent such contamination a preservative may be added to the solution, emulsion, or suspension; however, patient exposure to preservatives may have adverse effects to eye health.

The present disclosure provides one or more therapeutic agents formulated with a preservative capable of being removed by a preservative removing device of the present disclosure. Therapeutic agents may comprise compounds and salts, for use in the treatment of ophthalmic diseases. The disclosed compounds and salts can be used, for example, for the treatment or prevention of vision disorders and/or for use during ophthalmological procedures for the prevention and/or treatment of ophthalmic disorders. The following list of examples are not intended to be limiting.

In some embodiments, the therapeutic agent to be dispensed comprises an active ingredient selected from cyclosporine and lifitegrast. In some embodiments, the therapeutic agent may be an active ingredient in the treatment of dry eye.

In some embodiments, the at least one therapeutic agent to be dispensed comprises an active ingredient selected from sulfacetamide sodium, ofloxacin, gatifloxacin, ciprofloxacin, moxifloxacin, tobramycin, levofloxacin, prednisolone acetate, polymyxin B sulfate, and trimethoprim. In some embodiments, the therapeutic formulation to be dispensed comprises the active ingredients sulfacetamide sodium and prednisolone acetate. In some embodiments, the therapeutic formulation to be dispensed comprises the active ingredients polymyxin B sulfate and trimethoprim. In some embodiments, the therapeutic agent may be an active ingredient in the treatment of a bacterial infection.

In some embodiments, the at least one therapeutic agent to be dispensed comprises an active ingredient selected from brimonidine tartrate, bimatoprost, levobunolol hydrochloride, brinzolamide, betaxolol hydrochloride, pilocarpine hydrochloride, apraclonidine, travoprost, timolol maleate, latanoprost, dorzolamide hydrochloride, and tafluprost. In some embodiments, the therapeutic formulation to be dispensed comprises the active ingredients brimonidine tartrate and timolol maleate. In some embodiments, the therapeutic formulation to be dispensed comprises the active ingredients brinzolamide and brimonidine tartrate. In some embodiments, the therapeutic agent may be an active ingredient in the treatment of glaucoma or hypertension.

In some embodiments, the at least one therapeutic agent to be dispensed comprises an active ingredient selected from ketorolac tromethamine, fluorometholone, prednisolone acetate, difluprednate, fluorometholone acetate, nepafenac, dexamethasone, diclofenac sodium, bromfenac, gentamicin, tobramycin, neomycin, and polymyxin B sulfate. In some embodiments, the therapeutic formulation to be dispensed comprises the active ingredients gentamicin and prednisolone acetate. In some embodiments, the therapeutic formulation to be dispensed comprises the active ingredients tobramycin and dexamethasone. In some embodiments, the therapeutic formulation to be dispensed comprises the active ingredients neomycin, polymyxin B sulfate and dexamethasone. In some embodiments, the therapeutic agent may be an active ingredient in the treatment of inflammation.

In some embodiments, the at least one therapeutic agent to be dispensed comprises an active ingredient selected from nedocromil sodium, epinastine HCl, alcaftadine, lodoxamide tromethamine, emedastine difumarate, and olopatadine hydrochloride. In some embodiments, the therapeutic agent may be an active ingredient in the treatment of allergic conjunctivitis.

In some embodiments, the at least one therapeutic agent to be dispensed comprises an active ingredient selected from proparacaine hydrochloride and tetracaine hydrochloride. In some embodiments, the therapeutic agent may be a local anesthetic.

In some embodiments, the at least one therapeutic agent to be dispensed comprises an active ingredient selected from cyclopentolate hydrochloride, atropine sulfate, and tropicamide. In some embodiments, the therapeutic formulation to be dispensed comprises the active ingredients cyclopentolate hydrochloride and phenylephrine hydrochloride. In some embodiments, the therapeutic agent may dilate pupils.

In some embodiments, the at least one therapeutic agent to be dispensed comprises the active ingredient natamycin. In some embodiments, the therapeutic agent may be an active ingredient in the treatment of fungal infection.

In some embodiments, the at least one therapeutic agent to be dispensed comprises an active ingredient selected from lipoic acid choline ester chloride, rebamipide, pilocarpine, aceclidine, tropicamide, sodium hyaluronate, diclofenac sodium, pilocarpine HCl, and ketorolac. In some embodiments, the therapeutic formulation to be dispensed comprises the active ingredients aceclidine and tropicamide. In some embodiments, the therapeutic formulation to be dispensed comprises the active ingredients sodium hyaluronate and diclofenac sodium and pilocarpine HCl. In some embodiments, the therapeutic formulation to be dispensed comprises the active ingredients pilocarpine and ketorolac. In some embodiments, the therapeutic agent may be an active ingredient in the treatment of presbyopia.

In some cases, the therapeutic agent is a weak acid. Weak acids may undergo partial or incomplete dissociation in aqueous solution or water. Weak acids may generally be less attractive to the surface of the particulate plug, which is acidified by the fatty acid. The carboxylic acid functional groups of the fatty acid may increase hydrophilicity of the particulate plug while maintaining low affinity for the drug. The therapeutic agent may comprise a pKa of about 1 to about 14. The therapeutic agent may comprise a pKa of at least about 1. The therapeutic agent may comprise a pKa of at most about 14. The therapeutic agent may comprise a pKa of about 1 to about 3, about 1 to about 5, about 1 to about 7, about 1 to about 9, about 1 to about 11, about 1 to about 13, about 1 to about 14, about 3 to about 5, about 3 to about 7, about 3 to about 9, about 3 to about 11, about 3 to about 13, about 3 to about 14, about 5 to about 7, about 5 to about 9, about 5 to about 11, about 5 to about 13, about 5 to about 14, about 7 to about 9, about 7 to about 11, about 7 to about 13, about 7 to about 14, about 9 to about 11, about 9 to about 13, about 9 to about 14, about 11 to about 13, about 11 to about 14, or about 13 to about 14. The therapeutic agent may comprise a pKa of at least about 1, about 2, about 3, about 4, about 5, about 6, about 7, about 8, about 9, about 10, about 11, about 12, about 13, about 14, or about 14.

Illustrative solutions, emulsions, or suspensions which can be used in aspects of the pharmaceutical formulation disclosed herein are shown in Tables 1 to 4. Example solutions, emulsions, or suspensions in the table below may be integrated into preservative removing devices and methods of removing a preservative of the present disclosure. One or more embodiments, variations, and examples of the preservative removing devices, matrices, and methods described herein may be incorporated into an eye drop dispensing system, which system may comprise a squeezable bottle. A squeezable bottle may comprise a reservoir in which a fluid may be stored. A fluid stored in the reservoir may comprise an embodiment, variation, or example of solutions, emulsions, or suspensions described herein, including those examples provided in Tables 1 to 4.

TABLE 1

Pharmaceuticals Sorted by Indication

| Market Name | Drug | % Active Ingredient | Formulation Type | Indication | Preservative |
|---|---|---|---|---|---|
| Dry Eye | | | | | |
| Restasis | Cyclosporine | 0.05% | emulsion | keratoconjunctivitis sicca | none |
| Xiidra | Lifitegrast | 5% | solution | keratoconjunctivitis sicca | none |
| Visine | Tetrahydrozoline | | | keratoconjunctivitis sicca | |
| Bacterial Infection | | | | | |
| Bleph 10 | sulfacetamide sodium | 10% | solution | conjunctivitis and other ocular infections | benzalkonium chloride 0.005% |
| Blephamide | sulfacetamide sodium - prednisolone acetate | 10%/0.2% | suspension | bacterial ocular infection | benzalkonium chloride 0.004% |
| Ocuflox | Ofloxacin | 0.3% | solution | bacterial ocular infection; corneal ulcers | benzalkonium chloride (0.005%) |
| Polytrim | polymyxin B sulfate and trimethoprim | polymyxin B sulfate 10,000 units/mL; trimethoprim sulfate equivalent to 1 mg/mL | solution | ocular bacterial infections; conjunctivitis; blepharo-conjunctivitis | benzalkonium chloride 0.04 mg/mL |
| Zymaxid | Gatifloxacin | 0.3% and 0.5% | solution | bacterial conjunctivitis | benzalkonium chloride 0.005% |

TABLE 1-continued

Pharmaceuticals Sorted by Indication

| Market Name | Drug | % Active Ingredient | Formulation Type | Indication | Preservative |
|---|---|---|---|---|---|
| Zymar | Gatifloxacin | 0.3% | solution | bacterial conjunctivitis | benzalkonium chloride 0.005%; |
| Ciloxan | Ciprofloxacin | 0.3% | solution | bacterial conjunctivitis | None |
| Moxeza | Moxifloxacin | 0.5% | solution | bacterial conjunctivitis | none |
| Tobrex | Tobramycin | 0.3% | solution | infections of the eye and its adnexa caused by susceptible bacteria | benzalkonium chloride 0.01% |
| Vigamox | Moxifloxacin | 0.5% | solution | bacterial conjunctivitis | none |
| Iquix | Levofloxacin | 1.5% | solution | bacterial conjunctivitis | benzalkonium chloride 0.005% |
| Quixin | Levofloxacin | 0.5% | solution | bacterial conjunctivitis | benzalkonium chloride 0.005% |
| Glaucoma or Hypertension | | | | | |
| Alphagan | brimonidine tartrate | 0.01% | solution | open-angle glaucoma or ocular hypertension | Purite ® 0.005% (0.05 mg/mL) |
| Lumigan | Bimatoprost | 0.01% | solution | open angle glaucoma or ocular hypertension | benzalkonium chloride 0.2 mg/mL |
| Betagan | levobunolol hydrochloride | 0.5% | solution | chronic open-angle glaucoma or ocular hypertension | benzalkonium chloride 0.004% |
| Combigan | brimonidine tartrate/timolol maleate | 0.2%/0.5% | solution | glaucoma or ocular hypertension who require adjunctive or replacement therapy due to inadequately controlled IOP | benzalkonium chloride 0.005% |
| Azopt | Brinzolamide | 1% | suspension | ocular hypertension or open-angle glaucoma | benzalkonium chloride 0.1 mg |
| Betoptic S | betaxolol hydrochloride | 0.25% and 0.5% | suspension | ocular hypertension or chronic open angle glaucoma | benzalkonium chloride 0.1 mg in 1 mL |
| Isopto Carpine | pilocarpine hydrochloride | 1%, 2% and 4% | solution | IOP reduction; open-angle glaucoma or ocular hypertension; acute angle-closure glaucoma; induction of miosis | benzalkonium chloride 0.01% |
| Iopidine | Apraclonidine | 0.5% and 1.0% | solution | Short term adjunctive therapy in patients on maximally tolerated medical therapy who require additional IOP reduction | benzalkonium chloride 0.01% |
| Simbrinza | brinzolamide/ brimonidine tartrate | 1%/0.2% | suspension | reduction of elevated IOP in patients with open-angle glaucoma or ocular hypertension | benzalkonium chloride 0.03 mg |
| Travatan Z | Travoprost | 0.004% | solution | open-angle glaucoma or ocular hypertension who are intolerant of other intraocular pressure lowering medications | ionic buffered system, sofZia |
| Isralol | Timolol maleate | 0.5% | solution | ocular hypertension or open-angle glaucoma | benzalkonium chloride 0.05 mg/mL |

TABLE 1-continued

Pharmaceuticals Sorted by Indication

| Market Name | Drug | % Active Ingredient | Formulation Type | Indication | Preservative |
|---|---|---|---|---|---|
| Xalatan | Latanoprost | approximately 1.5 µg per drop | solution | open-angle glaucoma or ocular hypertension | benzalkonium chloride, 0.02% |
| Trusopt | dorzolamide hydrochloride | 2% | solution | ocular hypertension or open-angle glaucoma | benzalkonium chloride 0.0075% |
| Timoptic | timolol maleate | 0.25% and 0.5% | solution | ocular hypertension or open-angle glaucoma | benzalkonium chloride |
| Ziotan | Tafluprost | 0.0015% | solution | open-angle glaucoma or ocular hypertension | none |
| Vesneo | Latanoprostene Bunod | | | glaucoma | |
| Vyzulta | Latanoprostene Bunod | | | glaucoma | |
| Cosopt | Dorzolamide + Timolol | | | Glaucoma | |
| Inflammation | | | | | |
| Acular LS | ketorolac tromethamine | 0.4% | solution | ocular pain and burning/stinging following corneal refractive surgery | benzalkonium chloride 0.006% |
| Acular | ketorolac tromethamine | 0.5% | solution | inflammation following cataract surgery; relief of ocular itching due to seasonal allergic conjunctivitis | benzalkonium chloride 0.01% |
| Acuvail | ketorolac tromethamine | 0.45% | solution | treatment of pain and inflammation following cataract surgery | none |
| FML Forte | Fluorometholone | 0.25% | ointment | corticosteroid-responsive inflammation of the palpebral and bulbar conjunctiva, cornea and anterior segment of the globe | benzalkonium chloride 0.005% |
| FML | Fluorometholone | 0.1% | suspension | corticosteroid-responsive inflammation of the palpebral and bulbar conjunctiva, cornea and anterior segment of the globe | benzalkonium chloride 0.004% |
| Pred Forte | prednisolone acetate | 1% | suspension | steroid-responsive inflammation of the palpebral and bulbar conjunctiva, cornea, and anterior segment of the globe | benzalkonium chloride |
| Pred Mild | prednisolone acetate | 0.12% | suspension | mild to moderate noninfectious allergic and inflammatory disorders of the lid, conjunctiva, cornea, and sclera, including chemical and thermal burns | benzalkonium chloride |
| Pred-G | gentamicin and prednisolone acetate | 0.3%/1% | suspension | steroid-responsive inflammatory; bacterial infection; thermal burns or penetration of foreign bodies | Benzalkonium chloride 0.005% |
| Durezol | Difluprednate | 0.05% | emulsion | inflammation and pain associated with ocular surgery | sorbic acid 0.1% |

TABLE 1-continued

Pharmaceuticals Sorted by Indication

| Market Name | Drug | % Active Ingredient | Formulation Type | Indication | Preservative |
|---|---|---|---|---|---|
| Flarex | fluorometholone acetate | 0.1% | suspension | steroid-responsive inflammatory conditions of the palpebral and bulbar conjunctiva, cornea and anterior segment of the eye | benzalkonium chloride 0.01% |
| Ilevro | Nepafenac | 0.3% | suspension | pain and inflammation associated with cataract surgery | benzalkonium chloride 0.005% |
| Maxidex | Dexamethasone | 0.1% | suspension | Steroid responsive inflammatory conditions; corneal injury from chemical, radiation, or thermal burns, or penetration of foreign bodies | benzalkonium chloride 0.01% |
| Maxitrol | neomycin and polymyxin B sulfates and dexamethasone | neomycin sulfate equivalent to neomycin 3.5 mg, polymyxin B sulfate 10,000 units, dexamethasone 0.1% | solution | steroid-responsive inflammatory ocular conditions for which a corticosteroid is indicated and where bacterial infection or a risk of bacterial ocular infection exists | methylparaben 0.05%, propylparaben 0.01% |
| Nevanac | Nepafenac | 0.1% | suspension | pain and inflammation associated with cataract surgery | benzalkonium chloride 0.005% |
| Omnipred | prednisolone acetate | 1.0% | suspension | steroid responsive inflammatory conditions; corneal injury from chemical, radiation, or thermal burns, or penetration of foreign bodies | benzalkonium chloride 0.01% |
| Tobradex ST | tobramycin/ dexamethasone | 0.3%/0.05% | suspension | steroid-responsive inflammatory ocular conditions for which a corticosteroid is indicated and where superficial bacterial ocular infection exists | benzalkonium chloride 0.1 mg |
| Voltaren Ophthalmic | diclofenac sodium | 0.1% | solution | inflammation from cataract extraction; temporary relief of pain and photophobia following corneal refractive surgery | None |
| Bromday | Bromfenac | 0.09% | solution | postoperative inflammation in patients who have undergone cataract extraction | benzalkonium chloride 0.05 mg/mL |
| Xibrom | Bromfenac | 0.09% | solution | postoperative inflammation in patients who have undergone cataract extraction | benzalkonium chloride (0.05 mg/mL) |
| Xibrom | Bromfenac | 0.09% | solution | postoperative inflammation in patients who have undergone cataract extraction | benzalkonium chloride 0.05 mg/mL |

TABLE 1-continued

Pharmaceuticals Sorted by Indication

| Market Name | Drug | % Active Ingredient | Formulation Type | Indication | Preservative |
|---|---|---|---|---|---|
| Allergic Conjunctivitis | | | | | |
| Alocril | nedocromil sodium | 2% | solution | itching associated with allergic conjunctivitis | benzalkonium chloride 0.01% |
| Elestat | epinastine HCl | 0.05% | suspension | itching associated with allergic conjunctivitis | Benzalkonium chloride 0.01%; |
| Lastacaft | Alcaftadine | 0.25% | solution | itching associated with allergic conjunctivitis | benzalkonium chloride 0.005% |
| Alomide | lodoxamide tromethamine | 0.1% | solution | vernal keratoconjunctivitis; giant papillary conjunctivitis; allergic/atopic conjunctivitis | benzalkonium chloride 0.007% w/v |
| Emadine | emedastine difumarate | 0.5% | solution | allergic conjunctivitis | benzalkonium chloride, 0.01% |
| Pataday | olopatadine hydrochloride | 0.2% | solution | ocular itching associated with allergic conjunctivitis | benzalkonium chloride 0.01% |
| Pazeo | olopatadine hydrochloride | 0.7% | solution | ocular itching associated with allergic conjunctivitis | benzalkonium chloride 0.015% |
| Hair Growth | | | | | |
| Latisse | Bimatoprost | 0.03% | solution | hypotrichosis of the eyelashes | benzalkonium chloride 0.05 mg/mL |
| Local Anesthetic | | | | | |
| Alcaine | proparacaine hydrochloride | 0.5% | solution | topical anesthesia - removal of foreign bodies; measurement of intraocular pressure; conjunctive scraping procedures requiring a rapid and short acting topical ophthalmic anesthetic | benzalkonium chloride 0.01% |
| Tetracaine | Tetracaine hydrochloride | 0.5% | solution | | None |
| Pupil Dilation | | | | | |
| Cyclogyl | cyclopentolate hydrochloride | 0.5%, 1.0% or 2.0% | solution | pre- and post-operative states when mydriasis is required and when a shorter acting mydriatic and cycloplegic is needed in the therapy of iridocyclitis | Benzalkonium chloride 0.1 mg in 1.0 mL |
| Cyclomydril | cyclopentolate hydrochloride and phenylephrine hydrochloride | 0.2%/1.0% | solution | For the production of mydriasis (pupil dilation) | Benzalkonium chloride 0.01% |
| Isopto Atropine | atropine sulfate | 1% | solution | mydriasis; cycloplegia; penalization of the healthy eye in the treatment of amblyopia | benzalkonium chloride 0.01% |
| Mydriacyl | Tropicamide | 0.5% or 1.0% | solution | mydriasis and cycloplegia | benzalkonium chloride 0.01% |

TABLE 1-continued

Pharmaceuticals Sorted by Indication

| Market Name | Drug | % Active Ingredient | Formulation Type | Indication | Preservative |
|---|---|---|---|---|---|
| Fungal infection | | | | | |
| Natacyn | Natamycin | 5% | suspension | anti-fungal; fungal blepharitis, conjunctivitis, and keratitis | benzalkonium chloride 0.02% |

TABLE 2

Experimental Presbyopia Formulations.

| Drug Code | Drug | % Active Ingredient | Formulation Type | Indication | Preservative |
|---|---|---|---|---|---|
| Presbyopia | | | | | |
| EV06/ UNR844 | lipoic acid choline ester chloride | 3.0% | solution | presbyopia | benzalkonium chloride, 0.01% |
| PRX-100 | aceclidine/ tropicamide | 0.25-2.0%/ 0.025-0.1% | Solution or suspension | presbyopia | benzalkonium chloride, 0.02% |
| CSF-1 | sodium hyaluronate/ diclofenac sodium/ pilocarpine HCl | 0.1-0.9%/ 0.006-0.012%/ 0.2-0.4% | Solution or suspension | presbyopia | Any, benzalkonium chloride, 0.01% |
| AAGN- 199201 | Pilocarpine and/or oxymetazoline | 0.1%-1% | Solution or suspension | presbyopia | Any, benzalkonium chloride, 0.01% |
| AAGN- 190584 | ketorolac | 0.1%-1% | Solution or suspension | presbyopia | Any, benzalkonium chloride, 0.01% |

TABLE 3

Additional Pharmaceuticals

| Market Name | Drug | % Active Ingredient | Formulation Type | Indication | Preservative |
|---|---|---|---|---|---|
| Restasis | cyclosporine | 0.05% | emulsion | keratoconjunctivitis sicca | none |
| Latisse | bimatoprost | 0.03% | solution | hypotrichosis of the eyelashes | benzalkonium chloride 0.05 mg/mL |
| Alphagan | brimonidine Tartrate | 0.01% | solution | open-angle glaucoma or ocular hypertension | Purite ® 0.005% (0.05 mg/mL) |
| Lumigan | bimatoprost | 0.01% | solution | open angle glaucoma or ocular hypertension | benzalkonium chloride 0.2 mg/mL |
| Acular LS | ketorolac tromethamine | 0.4% | solution | ocular pain and burning/stinging following corneal refractive surgery | benzalkonium chloride 0.006% |
| Acular | ketorolac tromethamine | 0.5% | solution | inflammation following cataract surgery; relief of ocular itching due to seasonal allergic conjunctivitis | benzalkonium chloride 0.01% |
| Acuvail | ketorolac tromethamine | 0.45% | solution | treatment of pain and inflammation following cataract surgery | none |
| Alocril | nedocromil sodium | 2% | solution | itching associated with allergic conjunctivitis | benzalkonium chloride 0.01% |

TABLE 3-continued

Additional Pharmaceuticals

| Market Name | Drug | % Active Ingredient | Formulation Type | Indication | Preservative |
|---|---|---|---|---|---|
| Betagan | levobunolol hydrochloride | 0.5% | solution | chronic open-angle glaucoma or ocular hypertension | benzalkonium chloride 0.004% |
| Bleph 10 | sulfacetamide sodium | 10% | solution | conjunctivitis and other ocular infections | benzalkonium chloride 0.005% |
| Blephamide | sulfacetamide sodium-prednisolone acetate | 10%/0.2% | suspension | bacterial ocular infection | benzalkonium chloride 0.004% |
| Combigan | brimonidine tartrate/timolol maleate | 0.2%/0.5% | solution | glaucoma or ocular hypertension who require adjunctive or replacement therapy due to inadequately controlled iop | benzalkonium chloride 0.005% |
| Elestat | epinastine HCl | 0.05% | suspension | itching associated with allergic conjunctivitis | benzalkonium chloride 0.01%; |
| FML Forte | fluorometholone | 0.25% | ointment | corticosteroid-responsive inflammation of the palpebral and bulbar conjunctiva, cornea and anterior segment of the globe | benzalkonium chloride 0.005% |
| FML | fluorometholone | 0.1% | suspension | corticosteroid-responsive inflammation of the palpebral and bulbar conjunctiva, cornea and anterior segment of the globe | benzalkonium chloride 0.004% |
| Lastacaft | alcaftadine | 0.25% | solution | itching associated with allergic conjunctivitis | benzalkonium chloride 0.005% |
| Ocuflox | ofloxacin | 0.3% | solution | bacterial ocular infection; corneal ulcers | benzalkonium chloride (0.005%) |
| Polytrim | polymyxin B sulfate and trimethoprim | polymyxin B sulfate 10,000 units/mL; trimethoprim sulfate equivalent to 1 mg/mL | solution | ocular bacterial infections; conjunctivitis; blepharo-conjunctivitis | benzalkonium chloride 0.04 mg/mL |
| Pred Forte | prednisolone acetate | 1% | suspension | steroid-responsive inflammation of the palpebral and bulbar conjunctiva, cornea, and anterior segment of the globe | benzalkonium chloride |
| Pred Mild | prednisolone acetate | 0.12% | suspension | mild to moderate noninfectious allergic and inflammatory disorders of the lid, conjunctiva, cornea, and sclera, including chemical and thermal burns | benzalkonium chloride |
| Pred-G | gentamicin and prednisolone acetate | 0.3%/1% | suspension | steroid-responsive inflammatory; bacterial infection; thermal burns or penetration of foreign bodies | benzalkonium chloride or 0.005% |
| Zymaxid | gatifloxacin | 0.3% and 0.5% | solution | bacterial conjunctivitis | benzalkonium chloride 0.005% |
| Zymar | gatifloxacin | 0.3% | solution | bacterial conjunctivitis | benzalkonium chloride 0.005%; |
| Alcaine | proparacaine hydrochloride | 0.5% | solution | topical anesthesia-removal of foreign | benzalkonium chloride |

TABLE 3-continued

Additional Pharmaceuticals

| Market Name | Drug | % Active Ingredient | Formulation Type | Indication | Preservative |
|---|---|---|---|---|---|
| Alomide | lodoxamide tromethamine | 0.1% | solution | bodies; measurement of intraocular pressure; conjunctive scraping vernal keratoconjunctivitis; giant papillary conjunctivitis; allergic/atopic conjunctivitis | 0.01% benzalkonium chloride 0.007% w/v |
| Azopt | brinzolamide | 1% | suspension | ocular hypertension or open-angle glaucoma | benzalkonium chloride 0.1 mg |
| Betoptic S | betaxolol hydrochloride | 0.25% and 0.5% | suspension | ocular hypertension or chronic open angle glaucoma | benzalkonium chloride 0.1 mg in 1 mL |
| Ciloxan | ciprofloxacin | 0.3% | solution | bacterial conjunctivitis | None |
| Cyclogyl | cyclopentolate hydrochloride | 0.5%, 1.0% or 2.0% | solution | pre- and post-operative states when mydriasis is required and when a shorter acting mydriatic and cycloplegic is needed in the therapy of iridocyclitis | benzalkonium chloride 0.1 mg in 1.0 mL |
| Cyclomydril | cyclopentolate hydrochloride and phenylephrine hydrochloride | 0.2%/1.0% | solution | for the production of mydriasis (pupil dilation) | benzalkonium chloride 0.01% |
| Durezol | difluprednate | 0.05% | emulsion | inflammation and pain associated with ocular surgery | sorbic acid 0.1% |
| Emadine | emedastine difumarate | 0.5% | solution | allergic conjunctivitis | benzalkonium chloride, 0.01% |
| Flarex | fluorometholone acetate | 0.1% | suspension | steroid-responsive inflammatory conditions of the palpebral and bulbar conjunctiva, cornea and anterior segment of the eye | benzalkonium chloride 0.01% |
| Ilevro | nepafenac | 0.3% | suspension | pain and inflammation associated with cataract surgery | benzalkonium chloride 0.005% |
| Iopidine | apraclonidine | 0.5% and 1.0% | solution | short term adjunctive therapy in patients on maximally tolerated medical therapy who require additional iop reduction | benzalkonium chloride 0.01% |
| Isopto Atropine | atropine sulfate | 1% | solution | mydriasis; cycloplegia; penalization of the healthy eye in the treatment of amblyopia | benzalkonium chloride 0.01% |
| Isopto Carpine | pilocarpine hydrochloride | 1%, 2% and 4% | solution | iop reduction; open-angle glaucoma or ocular hypertension; acute angle-closure glaucoma; induction of miosis | benzalkonium chloride 0.01% |
| Maxidex | dexamethasone | 0.1% | suspension | steroid responsive inflammatory conditions; corneal injury from chemical, radiation, or thermal burns, or penetration of foreign bodies | benzalkonium chloride 0.01% |
| Maxitrol | neomycin and polymyxin B sulfates and | neomycin sulfate equivalent to | solution | steroid-responsive inflammatory ocular conditions for which | methylparaben 0.05%, propylparaben |

TABLE 3-continued

Additional Pharmaceuticals

| Market Name | Drug | % Active Ingredient | Formulation Type | Indication | Preservative |
|---|---|---|---|---|---|
| | dexamethasone | neomycin 3.5 mg, polymyxin B sulfate 10,000 units, dexamethasone 0.1% | | a corticosteroid is indicated and where bacterial infection or a risk of bacterial ocular infection exists | 0.01% |
| Moxeza | moxifloxacin | 0.5% | solution | bacterial conjunctivitis | None |
| Mydriacyl | tropicamide | 0.5% or 1.0% | solution | mydriasis and cycloplegia | benzalkonium chloride 0.01% |
| Natacyn | natamycin | 5% | suspension | anti-fungal; fungal blepharitis, conjunctivitis, and keratitis | benzalkonium chloride 0.02% |
| Nevanac | nepafenac | 0.1% | suspension | pain and inflammation associated with cataract surgery | benzalkonium chloride 0.005% |
| Omnipred | prednisolone acetate | 1.0% | suspension | steroid responsive inflammatory conditions; corneal injury from chemical, radiation, or thermal burns, or penetration of foreign bodies | benzalkonium chloride 0.01% |
| Pataday | olopatadine hydrochloride | 0.2% | solution | ocular itching associated with allergic conjunctivitis | benzalkonium chloride 0.01% |
| Pazeo | olopatadine hydrochloride | 0.7% | solution | ocular itching associated with allergic conjunctivitis | benzalkonium chloride 0.015% |
| Simbrinza | brinzolamide/ brimonidine tartrate | 1%/0.2% | suspension | reduction of elevated iop in patients with open-angle glaucoma or ocular hypertension | benzalkonium chloride 0.03 mg |
| Tetracaine | hydrochloride | 0.5% | solution | procedures requiring a rapid and shortacting topical ophthalmic anesthetic | None |
| Tobradex ST | tobramycin/ dexamethasone | 0.3%/0.05% | suspension | steroid-responsive inflammatory ocular conditions for which a corticosteroid is indicated and where superficial bacterial ocular infection exists | benzalkonium chloride 0.1 mg |
| Tobrex | tobramycin | 0.3% | solution | infections of the eye and its adnexa caused by susceptible bacteria | benzalkonium chloride 0.01% |
| Travatan Z | travoprost | 0.004% | solution | open-angle glaucoma or ocular hypertension who are intolerant of other intraocular pressure lowering medications | ionic buffered system, sofZia |
| Vigamox | moxifloxacin | 0.5% | solution | bacterial conjunctivitis | None |
| Voltaren Ophthalmic | diclofenac sodium | 0.1% | solution | inflammation from cataract extraction; temporary relief of pain and photophobia following corneal refractive surgery | None |
| Trusopt | dorzolamide hydrochloride | 2% | solution | ocular hypertension or open-angle glaucoma | benzalkonium chloride 0.0075% |
| Timoptic | timolol maleate | 0.25% and 0.5% | solution | ocular hypertension or open-angle glaucoma | benzalkonium chloride |

TABLE 3-continued

Additional Pharmaceuticals

| Market Name | Drug | % Active Ingredient | Formulation Type | Indication | Preservative |
|---|---|---|---|---|---|
| Ziotan | tafluprost | 0.0015% | solution | open-angle glaucoma or ocular hypertension | none |
| Xalatan | latanoprost | approximately 1.5 µg per drop | solution | open-angle glaucoma or ocular hypertension | benzalkonium chloride, 0.02% |
| Bromday | bromfenac | 0.09% | solution | postoperative inflammation in patients who have undergone cataract extraction | benzalkonium chloride 0.05 mg/mL |
| Isralol | timolol maleate | 0.5% | solution | ocular hypertension or open-angle glaucoma | benzalkonium chloride 0.05 mg/mL |
| Xibrom | bromfenac | 0.09% | solution | postoperative inflammation in patients who have undergone cataract extraction | benzalkonium chloride (0.05 mg/mL) |
| Iquix | levofloxacin | 1.5% | solution | bacterial conjunctivitis | benzalkonium chloride 0.005% |
| Quixin | levofloxacin | 0.5% | solution | bacterial conjunctivitis | benzalkonium chloride 0.005% |
| Xibrom | bromfenac | 0.09% | solution | postoperative inflammation in patients who have undergone cataract extraction | benzalkonium chloride 0.05 mg/mL |
| Xiidra | lifitegrast | 5% | solution | Dry Eye | None |

TABLE 4

Other Pharmaceuticals

| Code of Drug in Clinical Trial | Drug | % Active Ingredient | Formulation Type | Indication | Preservative |
|---|---|---|---|---|---|
| EV06/ UNR844 | lipoic acid choline ester chloride | 3.0% | solution | presbyopia | benzalkonium chloride, 0.01% |
| PRX-100 | aceclidine/ tropicamide | 0.25-2.0%/ 0.025-0.1% | Solution or suspension | presbyopia | benzalkonium chloride, 0.02% |
| SF-1 | sodium hyaluronate/ diclofenac sodium/ pilocarpine HCl | 0.1-0.9%/ 0.006-0.012%/ 0.2-0.4% | Solution or suspension | presbyopia | Any, benzalkonium chloride, 0.01% |
| ECF843 | | 0.1%-1% | Solution or suspension | Dry eye | Any, benzalkonium chloride, 0.01% |
| None | rebamipide | 1%, 2% | solution | Dry eye (keratoconjunctivitis sicca) | Any, benzalkonium chloride, 0.01% |
| AAGN-199201 | Pilocarpine and/or oxymetazoline | 0.1%-1% | Solution or suspension | presbyopia | Any, benzalkonium chloride, 0.01% |
| AAGN-190584 | ketorolac | 0.1%-1% | Solution or suspension | presbyopia | Any, benzalkonium chloride, 0.01% |
| | pilocarpine | 0.3% | Solution or suspension | presbyopia | Any, benzalkonium chloride, 0.01% |
| | pilocarpine | varies with severity of presbyopia, 0.3%-2.2% | Solution or suspension | presbyopia | Any, benzalkonium chloride, 0.01% |

Preservative

The present disclosure provides one or more preservatives for solutions, emulsions, or suspensions of therapeutic agents of the present disclosure. Preservatives may comprise compounds and salts, for use as preservatives for solutions, emulsions, or suspensions of therapeutic agents. The one or more preservatives may for example prevent microbial and/or fungal growth. The one or more preservatives may for example prevent physical or chemical deterioration of a therapeutic agent.

Non-limiting examples of preservative agents include benzalkonium chloride or bromide, ethylenediaminetetraacetic acid (EDTA), sodium salt of EDTA, chlorobutanol, phenylmercuric acetate, phenylmercuric nitrate, chlorhexidine acetate, thimerosal, benzethonium chloride, sorbic acid, alcohols, parabens (e.g., methylparaben, polyparaben), chlorhexidine, quaternary ammonium compounds, polyquaternium-1 (Polyquad®) Purite®, stabilized oxychloro complexes, Sofzia®, sodium perborate (GenAqua®), cetrimonium chloride, cetrimide, edetate disodium, etc. In some embodiments, a formulation of the disclosure does not include a preservative. In some embodiments, the preservative is benzalkonium chloride. In some embodiments, the preservative is a quaternary ammonium compound. In some embodiments, the preservative is polyquaternium-1. In some embodiments, the preservative is cetrimonium chloride.

In some embodiments, the particulate plug may further include a preservative removing compound or a preservative deactivating compound. Preservative removing or deactivating compounds can decrease toxicity of a formulation to be delivered through typical separation methods including, but not limited to, adsorption, ion exchange, chemical precipitation, or solvent extraction. Preservative removing or deactivating compounds can include, but are not limited to, activated charcoal, antioxidants, ethylenediaminetetraacetic acid (EDTA), anionic hydrogels, cationic compounds, neutralizing agents, or combinations thereof.

The Purite® preservative system includes Stabilized Oxychloro Complex (SOC), a combination of chlorine dioxide, chlorite, and chlorate. When exposed to light, SOC dissociates into water, oxygen, sodium and chlorine free radicals which cause oxidation of intracellular lipids and glutathione, interrupting vital enzymes for cell function and maintenance. For preservatives such as Purite® which produce chlorine free radicals, the particulate plug of the disclosure can include a material that has a high affinity for free radicals such as activated charcoal or antioxidants such as vitamin E.

The SofZia® preservative system in Travatan Z (Alcon Laboratories, Fort Worth, Tex.) contains borate, sorbitol, propylene glycol, and zinc. Without intending to be bound by theory, it is believed that the preservative effect is from a combination of borate and zinc. For preservatives including borate and zinc, such as SofZia®, the particulate plug of the disclosure can include a metal chelating agent such as EDTA, anionic hydrogels that can extract cationic zinc through electrostatic interactions, cationic hydrogels or resins that can extract anionic borate ions through electrostatic interactions, or a neutralizing agent that can neutralize boric acid.

The materials that can sequester the preservative can be incorporated into the particulate plug as microparticles, such as particles of activated charcoal. The microparticles can be packed into the particulate plug such that the liquid has sufficient space in between the particles to flow out, while also providing sufficient contact area for binding. Alternatively, the sequestering materials could be incorporated into particles of other suitable materials such as the polymer particles of the disclosure to facilitate the contact between the eluding formulation and the sequestering material. In some cases, the sequestration material, can be integrated into the polymer covalently. For example, negative ions that can complex with zinc could be incorporated into polymers. The sequestering material can be a nanoparticle or can be incorporated into a nanoparticle, which could in turn be dispersed into the polymer particles that form a packed bed in the tip. The nanoparticle could also be deposited just on the surface of the larger particles. The sequestering material could also form tubes that can be arranged in parallel to provide the path for liquid to flow out and sequestration to occur on the surface.

The materials present in the particulate plug to neutralize the free radicals in the formulation, for example, vitamins, can be incorporated into the polymer particles that form the particulate plug. Bases can be incorporated to bring the pH to a level that is comfortable in the eyes. The polymer particles can be loaded with vitamin E for example by soaking the particles in a solution of vitamin E dissolved in an organic liquid, leading to uptake of vitamin E into the particles. Subsequently, the organic liquid such as ethanol can be evaporated or extracted into water to form particles loaded with vitamin E. The material of the particles that is loaded with vitamin E could be chosen to achieve other beneficial purposes such as extraction of some other component of the preservative. Bases could be directly integrated into the hydrogel preparations.

The preservative effect of the formulations can be improved by incorporation of another preservative such as Benzalkonium Chloride so that the formulation can pass EPA criterion as well. The added BAK or the other preservative can be removed by the particulate plug to achieve improved preservative performance without increasing toxicity.

The particulate plug including a preservative removing compound or preservative deactivating compound can be formed in various shapes such as spheres, cylinders, tubes, highly irregular, flat sheets etc, where the surface could be rough or smooth. The particles or other shapes integrated into the tip can contain some preservative to ensure that the tip itself remains sterile. The preservative pre-loaded into the tip could be loaded via adsorption or be chemically attached to the material through a bond. For example, Polyquaternium can be integrated into the polymer forming the particles. The covalent attachment will prevent diffusion of the pre-loaded preservative into the tear film. Alternatively, the pre-loaded preservative could be sufficiently large in molecular weight or have very low partitioning into the eluding formulation.

In cases wherein the particulate plug including a preservative removing compound or a preservative deactivating compound is intended to add a component to the eluding formulation, the amount of that material in the particulate plug will be sufficiently large to ensure that there is sufficient amount remaining for the entire bottle, or at least 90% of the bottle. In cases wherein the particulate plug including a preservative removing compound or a preservative deactivating compound is intended to sequester a component from the eluding formulation, the volume and area in the particulate plug will be sufficiently large to sequester the desired component from at least 90% of the formulation in the bottle.

The present disclosure provides salts of any one or both of a therapeutic agent and a preservative. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt.

Metal salts can arise from the addition of an inorganic base to a compound of the present disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Acid addition salts can arise from the addition of an acid to a compound of the present disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucuronic acid, saccharic acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucuronate salt, a saccharate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Solution, Emulsion, or Suspension

Provided herein are solutions, emulsions, or suspensions of a therapeutic agent and a preservative. In some embodiments, provided herein are compositions comprising a therapeutically effective amount of any compound or salt of any one of the preservatives and/or therapeutic agents of the present disclosure. In some embodiments, a therapeutic solution, emulsion, or suspension may be used in any of the methods described herein. The solution, emulsion, or suspension may additionally comprise one or more pharmaceutically acceptable excipients.

In some embodiments, a compound of preservative and/or therapeutic agent may be used for the treatment of a therapeutic disorder such as, dry eye, bacterial infection, glaucoma, hypertension, inflammation, allergic conjunctivitis, hypotrichosis of the eyelashes, fungal infection, etc. Additionally, or alternatively, a compound of a preservative and/or therapeutic agent may be used during a preventative, diagnostic, or therapeutic ophthalmological procedure, for example, local anesthetic, pupil dilation, etc. A formulation administered to the eye may be administered topically, for example, with an eye drop.

A compound of the therapeutic agent described herein can be present in a solution, emulsion, or suspension of the present disclosure at a concentration of, for example, about 500 nanomolar (nM), about 600 nM, about 700 nM, about 800 nM, about 900 nM, about 1 micromolar (µM), about 2 µM, about 3 µM, about 4 µM, about 5 µM, about 6 µM, about 7 µM, about 8 µM, about 9 µM, about 10 µM, about 20 µM, about 30 µM, about 40 µM, about 50 µM, about 60 µM, about 70 µM, about 80 µM, about 90 µM, about 100 µM, about 150 µM, about 200 µM, about 250 µM, about 300 µM, about 350 µM, about 400 µM, about 450 µM, about 500 µM, about 550 µM, about 600 µM, about 650 µM, about 700 µM, about 750 µM, about 800 µM, about 850 µM, about 900 µM, about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 millimolar (mM). The compound of a therapeutic agent described herein may be present in a solution, emulsion, or suspension within a range of concentrations, the range being defined by an upper and lower value selected from any of the preceding concentrations. For example, the compound or salt of a therapeutic agent of the disclosure may be present in the solution, emulsion, or suspension at a concentration of from about 1 nM to about 100 mM, about 10 nM to about 10 mM, about 100 nM to about 1 mM, about 500 nM to about 1 mM, about 1 mM to about 50 mM, about 10 mM to about 40 mM, about 20 mM to about 35 mM, or about 20 mM to about 30 mM.

In some embodiments, a solution, emulsion, or suspension such as an aqueous solution of the disclosure, comprises from about 0.001 weight percent (wt %) to about 0.3 wt % of the compound of any one of the preservatives disclosed herein. In some embodiments, a solution, emulsion, or suspension such as an aqueous solution of the disclosure, comprises about 0.001 wt %, about 0.002 wt %, about 0.003 wt %, about 0.004 wt %, about 0.005 wt %, about 0.006 wt %, about 0.007 wt %, about 0.008 wt %, about 0.009 wt %, about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2 wt %, about 3 wt %, about 4 wt %, about 5 wt %, about 6 wt %, about 7 wt %, about 8 wt %, about 9 wt %, or about 10 wt % of a compound of the preservative described herein.

The preservative described herein can be present in a solution, emulsion, or suspension of the present disclosure at a concentration of, for example, about 500 nM, about 600 nM, about 700 nM, about 800 nM, about 900 nM, about 1 µM, about 2 µM, about 3 µM, about 4 µM, about 5 µM, about 6 µM, about 7 µM, about 8 µM, about 9 µM, about 10 µM, about 20 µM, about 30 µM, about 40 µM, about 50 µM, about 60 µM, about 70 µM, about 80 µM, about 90 µM, about 100 µM, about 150 µM, about 200 µM, about 250 µM, about 300 µM, about 350 µM, about 400 µM, about 450 µM, about 500 µM, about 550 µM, about 600 µM, about 650 µM, about 700 µM, about 750 µM, about 800 µM, about 850 µM, about 900 µM, about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. The compound of a preservative described herein may be present in a composition within a range of concentrations, the range being defined by an upper and lower value selected from any of the preceding concentrations. For example, the compound of a preservative of the disclosure may be present in the solution, emulsion, or suspension at a concentration of from about 1 nM to about 100 mM, about 10 nM to about 10 mM, about 100 nM to about 1 mM, about 500 nM to about 1 mM, about 1 mM to about 50 mM, about 10 mM to about 40 mM, about 20 mM to about 35 mM, or about 20 mM to about 30 mM.

Solutions, emulsions, or suspensions of the disclosure can be formulated at any suitable pH. In some embodiments, the pH of the solution emulsion or suspension is about 4, about 4.05, about 4.1, about 4.15, about 4.2, about 4.25, about 4.3, about 4.35, about 4.4, about 4.45, about 4.5, about 4.55, about 4.6, about 4.65, about 4.7, about 4.75, about 4.8, about 4.85, about 4.9, about 4.95, about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.8, about 8.9, or about 9 pH units. In some embodiments, the pH of the solution, emulsion, or suspension is from about 4 to about 10, about 5 to about 9, about 6 to about 8, about 6.5 to about 8, about 6 to about 7, about 6.2 to about 7.4, about 6.2 to about 7.8, about 6.3 to about 7.5, or about 6.75 to about 7.1. In some embodiments the pH of the solution, emulsion, or suspension is about 6.9.

In some embodiments, solutions, emulsions, or suspensions of the present disclosure further comprise one or more physiologically acceptable carriers including excipients and auxiliaries which facilitate processing of the pharmaceutical agent into preparations which are used pharmaceutically. Proper formulation is dependent upon the route of administration chosen.

In some embodiments, the addition of an excipient to a pharmaceutical formulation of the present disclosure can increase or decrease the viscosity of the composition by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. In some embodiments, the addition of an excipient to a pharmaceutical formulation of the present disclosure can increase or decrease the viscosity of the composition by no greater than 5%, no greater than 10%, no greater than 15%, no greater than 20%, no greater than 25%, no greater than 30%, no greater than 35%, no greater than 40%, no greater than 45%, no greater than 50%, no greater than 55%, no greater than 60%, no greater than 65%, no greater than 70%, no greater than 75%, no greater than 80%, no greater than 85%, no greater than 90%, no greater than 95%, or no greater than 99%. Examples of ranges which the viscosity change falls within can be created by combining any two of the preceding percentages. For example, the addition of an excipient can increase or decrease the viscosity of the composition by 5% to 99%, by 10% to 95%, by 20% to 70% or by 35% to 55%.

In some embodiments, solutions, emulsions, or suspensions of the present disclosure further comprise an agent for adjusting the osmolarity of the solution, emulsion, or suspension, e.g., mannitol, sodium chloride, sodium sulfate, dextrose, potassium chloride, glycerin, propylene glycol, calcium chloride, and magnesium chloride. In some embodiments, the solution, emulsion, or suspension comprises from about 0.1 wt % to about 10 wt %, about 0.5 wt % to about 8 wt %, about 1 wt % to about 5 wt %, about 1 wt % to about 4 wt %, or about 1 wt % to about 3 wt % of an agent for adjusting the osmolarity of the solution, emulsion, or suspension. In some embodiments, the solution, emulsion, or suspension of the disclosure has an osmolarity from about 10 milliosmoles (mOsm) to about 1000 mOsm, about 100 mOsm to about 700 mOsm, about 200 mOsm to about 400 mOsm, about 200 mOsm to about 300 mOsm or even about 250 mOsm to about 310 mOsm. In some embodiments, the osmolality is about 270 mOsm.

The amount of the excipient in a solution, emulsion, or suspension of the present disclosure can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 55% about 60%, about 65%, about 70%, about 75%, about 80%, about 85%, about 90%, about 95%, about 99%, or about 100% by mass or by volume of the unit dosage form. The amount of the excipient in a solution, emulsion, or suspension can be between 0.01% and 1000%, between 0.02% and 500%, between 0.1% and 100%, between 1% and 50%, between 0.01% and 1%, between 1% and 10%, between 10% and 100%, between 50% and 150%, between 100% and 500%, or between 500% and 1000% by mass or by volume of the unit dosage form.

The ratio of a compound of a therapeutic agent of the present disclosure to an excipient in a pharmaceutical formulation of the present disclosure can be about 100:about 1, about 95:about 1, about 90:about 1, about 85:about 1, about 80:about 1, about 75:about 1, about 70:about 1, about 65:about 1, about 60:about 1, about 55:about 1, about 50:about 1, about 45:about 1, about 40:about 1, about 35:about 1 about 30:about 1, about 25:about 1, about 20:about 1, about 15:about 1, about 10:about 1, about 9:about 1, about 8:about 1, about 7:about 1, about 6:about 1, about 5:about 1, about 4:about 1, about 3:about 1, about 2:about 1, about 1:about 1, about 1:about 2, about 1:about 3, about 1:about 4, about 1:about 5, about 1:about 6, about 1:about 7, about 1:about 8, about 1:about 9, or about 1:about 10. The ratio of a compound of a therapeutic agent to an excipient in a solution, emulsion, or suspension of the present disclosure can be within the range of between about 100:about 1 and about 1 to about 10, between about 10:about 1 and about 1:about 1, between about 5:about 1 and about 2:about 1.

Pharmaceutically acceptable carriers are well known in the art and include, for example, aqueous solutions such as water or physiologically buffered saline or other solvents or vehicles such as glycols, glycerol, oils such as olive oil, or organic esters. The excipients can be chosen, for example, to effect delayed release of an agent or to selectively target one or more cells, tissues or organs. The composition can also be present in a solution suitable for topical administration, such as an eye drop.

Pharmaceutically acceptable stabilizers present in the solution, emulsion, or suspension may comprise one or more of the following: sodium thiosulfate pentahydrate (or any other salt or hydrate of thiosulfate), sodium iodide (or any other salt or hydrate of iodide), sodium sulfate (or any other salt or hydrate of sulfate), or xanthan gum.

In some embodiments, the solution emulsion or suspension provided herein comprises an alcohol as an excipient. Non-limiting examples of alcohols include ethanol, propylene glycol, glycerol, polyethylene glycol, chlorobutanol, isopropanol, xylitol, sorbitol, maltitol, erythritol, threitol, arabitol, ribitol, mannitol, galactilol, fucitol, lactitol, and combinations thereof.

Methods for the preparation of compositions comprising the compounds described herein can include formulating the compounds with one or more inert, pharmaceutically-acceptable excipients. Liquid compositions include, for example, solutions in which a compound is dissolved, emulsions comprising a compound, or a solution containing liposomes, micelles, or nanoparticles comprising a compound as disclosed herein. These compositions can also contain minor amounts of nontoxic, auxiliary substances, such as wetting or emulsifying agents, pH buffering agents, and other pharmaceutically-acceptable additives.

EXAMPLES

Example 1

20/80 Polypropylene Stearic Acid Blend

A blend was made with isotactic Polypropylene from Sigma Aldrich (Lot MKCH9443) avg MW—250,000 and 97% Stearic acid from Acros Organics (Lot A0404313). A 20/80 weight to weight (w/w) blend was made by adding 2.0 grams (g) of Polypropylene to 8.0 g of Stearic acid in a 20 milliliters (mL) scintillation vial. This was slowly heated while stirring. The viscosity of the mixture allowed it to be poured into cool, stirred water. Water was decanted and the material placed under vacuum to dry. The material was then crushed in a grinder and sieved to <500 micron (ptm) particles. BAK uptake was initially tested by adding 0.2 g of powder to 5 mL of 1000 parts per million (ppm) United States Pharmacopeia grade BAK solution. This was stirred for 2 days, filtered, and analyzed by high performance liquid chromatography (HPLC) to calculate a BAK partition coefficient of 350 for this material. Labeled: 2NB78A in the tables herein.

A Timolol Maleate/Brimonidine tartrate ophthalmic solution was prepared (e.g., 2NB62, a Combigan analogue, etc) according to Table 5. The following were added to a 500 mL bottle: 2.151 g of Sodium Phosphate dibasic heptahydrate (Fisher Chemical L #187384), 0.432 g of Sodium Phosphate monobasic monohydrate (Fisher Chemical L #188731), 0.505 g of 0.991% BAK solution (Lot 2NB61), 0.202 g of Brimonidine Tartrate (BOC Sciences L #BV19V06171), and 0.681 g of Timolol Maleate (BOC Sciences L #BS19V04062). Ultra-pure water (100.017 g) of was added and stirred on a rotary shaker overnight to dissolve. Three mL of the solution, 2NB62, was placed into a 5 mL dropper bottle. Stearic acid/polypropylene powder (0.32 g) was loaded into a proprietary testing tip. The tip was then placed on the dropper bottle containing the solution.

TABLE 5

Timolol Maleate/Brimonidine tartrate ophthalmic solution

| TC-Combigan 2NB62 Ingredient | Conc % (w/v) |
|---|---|
| Brimonidine Tartrate | 0.2 |
| Timolol Maleate | 0.68 |
| BAK (70/30 C12/C14)339.992/368.046 | 0.005 |
| Sodium Phosphate monobasic monohydrate | 0.43 |
| Sodium Phosphate dibasic heptahydrate | 2.15 |
| Sodium hydroxide | |
| Hydrochloric acid | |
| mOsm (Total Ionization) | |
| pH measured | 6.9 |
| mOsm Measured (Vapro 5520) | 272 |

In a simulated usage, two drops are dispensed and diluted according to the proper method for HPLC analysis. Additional pairs of drops are dispensed at intervals no less than 1 hour (hr) apart. A standard consisting of the starting material is taken and diluted according to the specific HPLC method. Then each individual drop is analyzed on the HPLC. The uptake is determined by comparing the area counts from the HPLC peaks of the starting solution to the area counts of the drop. Results show (Table 6) that neither the concentration of Timolol nor Brimonidine are significantly affected from passing through the powder in the tip.

TABLE 6

Timolol Maleate/Brimonidine tartrate API uptake test

| Sample Description | Sample # | Drop # | Timolol % Uptake | Brimonidine % Uptake | Drops mass (g) | Date and Time | Timolol ppm/area counts | Brimonidine counts ppm/area |
|---|---|---|---|---|---|---|---|---|
| Combigan Mimic pH 6.9 | 2NB62 | | | | | | 158887.0 | 115132.5 |
| 20/80 Polypropylene/ Stearic Acid Melt <500 µm particle size | 2NB78A | 1 | 2% | 2% | 0.0821 | Oct. 3, 2019 9:30 | 154924.5 | 113302.5 |
| | | 2 | 2% | 2% | 0.0849 | Oct. 3, 2019 10:30 | 156203.0 | 112807.5 |
| | | 3 | 2% | 2% | 0.0803 | Oct. 3, 2019 11:30 | 155159.0 | 112309.5 |
| | | 4 | 2% | 2% | 0.0724 | Oct. 3, 2019 12:30 | 155777.5 | 112658.5 |
| | | 5 | 1% | 2% | 0.0814 | Oct. 3, 2019 13:30 | 156526.0 | 112971.5 |
| | | 6 | 2% | 2% | 0.0862 | Oct. 3, 2019 14:30 | 156382.5 | 113301.0 |
| | | 8 | 3% | 2% | 0.0798 | Oct. 4, 2019 10:30 | 153459.0 | 112416.0 |
| | | 9 | 2% | 2% | 0.0805 | Oct. 4, 2019 11:30 | 155739.0 | 113253.0 |

A separate, parallel drop test was performed using the same materials to test BAK uptake. The separate drop test was performed since the dilution and UV signal strength are vastly different. In the data below (Table 7) only the first drop contains about 5% of the starting BAK. In successive drops, the BAK is not detected (e.g., is undetectable, is below a detectable threshold based on UV absorption, etc.).

TABLE 7

Timolol Maleate/Brimonidine tartrate BAK uptake test

| Sample Description | Sample # | Drop Number | BAK C-12 remaining | BAK C-14 remaining | Drops mass (g) | ACN weight |
|---|---|---|---|---|---|---|
| Combigan Mimic. Right phosphate buffers | 2NB62 | | Starting: 35 ppm | Starting: 15 ppm | | |
| 20/80 Polypropylene/Stearic Acid Melt Blend <500 μm | 2NB78A | 1 | 8% | 3% | 0.0744 | 0.0744 |
| | | 2 | 0% | 0% | 0.0725 | 0.0722 |
| | | 3 | 0% | 0% | 0.0827 | 0.0824 |
| | | 4 | 0% | 0% | 0.0569 | 0.0594 |
| | | 5 | 0% | 0% | 0.0838 | 0.0837 |
| | | 6 | 0% | 0% | 0.086 | 0.086 |
| | | 7 | 0% | 0% | 0.085 | 0.0855 |

Example 2

Recrystallized Stearic Acid 15 g of 97% stearic acid (Acros organics Lot #A0404313) was added to 300 mL of acetone and heated to 40° C. to dissolve. The solution was allowed to cool to room temperature as stearic acid crystallized out of solution. The solution was refrigerated for two hours to complete. The stearic acid formed flakes that were removed by filtration. The recrystallized stearic acid was dried at room temperature under vacuum overnight.

Bimatoprost ophthalmic solution (20 mL) was formulated by combining 0.0027 g of Citric Acid Anhydrous (Alfa Aesar L #X16D073), 0.0536 g of Sodium phosphate dibasic, heptahydrate (Fisher chemical L #187384) and 0.1619 g of Sodium Chloride (Fisher chemical L #177082) to 20 g stock solution (2NB70.1) of 300 ppm Bimatoprost and 50 ppm BAK.

Bimatoprost formulation (3 mL), was placed into a 5 mL dropper bottle. Recrystallized Stearic acid flakes (0.116 g) was loaded into a proprietary testing tip. The tip was then placed on the dropper bottle containing the solution.

In a simulated usage, two drops are dispensed and diluted according to the proper method for HPLC analysis. Additional pairs of drops are dispensed at intervals no less than 1 hour apart. A standard consisting of the starting material is taken and diluted according to the specific HPLC method. Then each pair of drops was analyzed on the HPLC. The uptake is determined by comparing the area counts of the starting solution to the area counts of the drop. Bimatoprost has a similar linear signal range as BAK in this formulation so all data is collected from a single drop test. Results (Table 8) show that Bimatoprost is not significantly reduced while BAK is eliminated from passing through the recrystallized stearic acid flakes. In successive drops, the BAK is not detected (e.g., is undetectable, is below a detectable threshold based on UV absorption, etc.).

TABLE 8

| | | | | | | | | | | | |
|---|---|---|---|---|---|---|---|---|---|---|---|
| Sample Description | Sample # | Drop # | Brimonidine % Uptake | BAK C-12 remaining | BAK C-14 remaining | Drops mass (g) | CAN weight | Date and Time | Bimatopropst Area count | BAK C-12 area count | BAK C-14 area count |
| Bimatoprost mimic proper buffer 300 ppm and 50 ppm BAK (from 2NB70.1) | 2NB76 | | | | | | | | 616041 | 47926 | 18306 |
| Recrystallized Stearic Acid Tip mass: 0.116 g | 2NB77 | 1 | −4% | 1% | 0% | 0.0651 | 0.0651 | Sep. 27, 2019 9:45 | 641157 | 2846 | 0 |
| | | 2 | 3% | 0% | 0% | 0.0700 | 0.0700 | Sep. 27, 2019 10:45 | 398907 | 0 | 0 |
| | | 3 | −3% | 0% | 0% | 0.0550 | 0.0550 | Sep. 27, 2019 11:45 | 641620 | 0 | 0 |
| | | 4 | −5% | 0% | 0% | 0.0620 | 0.0620 | Sep. 27, 2019 13:45 | 642164 | 0 | 0 |
| | | 5 | 0% | 0% | 0% | 0.0705 | 0.0705 | Sep. 27, 2019 14:45 | 613921 | 0 | 0 |
| | | 6 | −2% | 0% | 0% | 0.0736 | 0.0736 | Sep. 27, 2019 15:45 | 623469 | 0 | 0 |
| | | 7 | 2% | 0% | 0% | 0.0595 | 0.0595 | Sep. 30, 2019 14:20 | 605200 | 0 | 0 |
| | | 8 | 0% | 0% | 0% | 0.0733 | 0.0733 | Sep. 30, 2019 15:20 | 608248 | 0 | 0 |
| | | 9 | 1% | 0% | 0% | 0.0752 | 0.0752 | Sep. 30, 2019 16:20 | 604491 | 0 | 0 |

TABLE 8-continued

Bimatoprost API/BAK uptake test

| Sample Description | Sample # | Drop # | Brimonidine % Uptake | BAK C-12 remaining | BAK C-14 remaining | Drops mass (g) | CAN weight | Date and Time | Bimatopropst Area count | BAK C-12 area count | BAK C-14 area count |
|---|---|---|---|---|---|---|---|---|---|---|---|
| | | 10 | −1% | 0% | 0% | 0.0725 | 0.0734 | Oct. 1, 2019 8:00 | 613257 | 0 | 0 |
| | | 11 | 1% | 0% | 0% | 0.0619 | 0.0619 | Oct. 1, 2019 9:00 | 609290 | 0 | 0 |

Example 3

50/50 Polypropylene Stearic Acid Blend

In a 20 mL Scintillation vial, 5.0 g of Polypropylene Isotactic Mw 250000 Aldrich 427888 lot MKCH$_{9443}$) was combined with 5.0 g of 97% Stearic acid from Acros (Lot A0404313). This mixture was heated to a melt while stirring. Mixing was difficult due to the viscosity. The material was spatulated into water. Due to high viscosity it could not be poured. This material was removed from the water and briefly dried in a vacuum for 2 hours. This was placed into a rotary blade grinder and reduced to powder. The resulting material was sieved to 63-500 μm.

A Lifitegrast ophthalmic solution (e.g., Xiidra mimic in the table) was prepared, consisting of 5.0% Lifitegrast (BOC Sciences Lot B19V08071), 2.0% Sodium Phosphate Dibasic Anhydrous (J. T. Baker Lot 0000236665), 0.5% Sodium thiosulfate pentahydrate (Fisher Chemical Lot 181801), and 0.005% BAK Aldrich 12063 (Lot #BCBW4741).

Three mL of the Lifitegrast formulation was placed into a 5 mL dropper bottle. 50/50 polypropylene/steric acid blend (0.328 g) was loaded into a proprietary testing tip. The tip was then placed on the dropper bottle containing the solution.

In a simulated usage, two drops are dispensed and diluted according to the proper method for HPLC analysis. Due to the relatively high concentration of Lifitegrast, 2 separate drops tests were done for the active pharmaceutical ingredient and BAK. A standard consisting of the starting material is taken and diluted according to the specific HPLC method. Then each pair of drops was analyzed on the HPLC. The uptake is determined by comparing the area counts of the HPLC peaks of the starting solution to the area counts of the drop.

TABLE 9

Lifitegrast API uptake test

| Sample Description | Sample # | Drop Number | Lifitegrast % Uptake | (2) Drops mass (g) | Date and Time | Tip Mass | Lifitegrast Area counts #1 | Lifitegrast Area counts #1 |
|---|---|---|---|---|---|---|---|---|
| Xiidra Mimic: 2% Na$_2$PO$_4$ 0.05% Na$_2$S$_2$O$_3$ 50 ppm BAK mOsm-415 | 2NB84D | | | | | | 1223094 | 1229995 |
| 50/50 PP/SA 63-500 μm | 2TC69 | 1 | 0% | 0.0672 | Nov. 4, 2019 8:35 | 0.328 | 1211452 | 1212829 |
| | | 2 | 1% | 0.0755 | Nov. 4, 2019 9:35 | | 1199836 | 1202356 |
| | | 3 | 1% | 0.0711 | Nov. 4, 2019 10:35 | | 1202471 | 1204737 |
| | | 4 | 0% | 0.0723 | Nov. 4, 2019 11:35 | | 1209839 | 1211933 |
| | | 5 | 0% | 0.0716 | Nov. 4, 2019 12:35 | | 1211852 | 1210927 |
| | | 6 | 0% | 0.0706 | Nov. 4, 2019 13:35 | | 1211335 | 1211229 |

TABLE 10

Lifitegrast BAK uptake test

| Sample Description | Sample # | Drop # | BAK C-12 remaining | BAK C-14 remaining | (2) Drops mass (g) | ACN weight | Date and Time | BAK C-12 area count | BAK C-14 area count |
|---|---|---|---|---|---|---|---|---|---|
| Xiidra Mimic: 2% Na$_2$PO$_4$ 0.05% Na$_2$S$_2$O$_3$ 50 ppm BAK mOsm-415 | 2NB84D | | Starting: 35 ppm | Starting: 15 ppm | | | | 39466 | 18427 |
| 50/50 PP/SA 63-500 μm | 2TC69 | 1 | 33% | 19% | 0.0586 | 0.0579 | Oct. 31, 2019 10:00 | 13234 | 3610 |

TABLE 10-continued

Lifitegrast BAK uptake test

| Sample Description | Sample # | Drop # | BAK C-12 remaining | BAK C-14 remaining | (2) Drops mass (g) | ACN weight | Date and Time | BAK C-12 area count | BAK C-14 area count |
|---|---|---|---|---|---|---|---|---|---|
| | | 2 | 3% | 0% | 0.0690 | 0.0691 | Oct. 31, 2019 11:00 | 1102 | 0 |
| | | 3 | 0% | 0% | 0.0692 | 0.0692 | Oct. 31, 2019 12:00 | 0 | 0 |
| | | 4 | 0% | 0% | 0.0693 | 0.0693 | Oct. 31, 2019 13:00 | 0 | 0 |
| | | 5 | 0% | 0% | 0.0634 | 0.0638 | Oct. 31, 2019 14:00 | 0 | 0 |
| | | 6 | 0% | 0% | 0.0625 | 0.0645 | Oct. 31, 2019 15:00 | 0 | 0 |

In the HPLC data (Table 9 and 10) it can be seen that the Lifitegrast was not hindered while only a small amount of BAK came through on the first drop only and was not detectable in later drops. After the first drop, the BAK is not detected (e.g., is undetectable, is below a detectable threshold based on comparison of the area counts of the HPLC peaks of the starting solution to the area counts of the drop, etc.).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the disclosure described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A particulate plug for removing a preservative from a solution, suspension, or emulsion comprising a drug, the particulate plug comprising microparticles of a hydrophobic polymer/fatty acid blend, wherein the microparticles form a particulate plug capable of being fitted to an outlet of a container for the solution, emulsion, or suspension, wherein the particulate plug selectively removes a preservative from the solution, emulsion, or suspension, wherein the drug is lifitegrast.

2. The particulate plug of claim 1, wherein the microparticles have a dimension of 5 μm to about 10,000 μm.

3. The particulate plug of claim 1, wherein the preservative comprises benzalkonium chloride (BAK).

4. The particulate plug of claim 1, wherein the hydrophobic polymer/fatty acid blend comprises a hydrophobic polymer selected from the group consisting of isotactic polypropylene, low density polyethylene, and high density polyethylene.

5. The particulate plug of claim 4, wherein the isotactic polypropylene has an average MW of about 250,000.

6. The particulate plug of claim 4, wherein the isotactic polypropylene has an average MW of about 100,000 to about 300,000.

7. The particulate plug of claim 4, wherein the isotactic polypropylene has an average MW of greater than 300,000.

8. The particulate plug of claim 1, wherein the hydrophobic polymer/fatty acid blend comprises a hydrophobic polymer selected from the group consisting of homopolymers of ethylene, propylene, 1-butene, 4-methyl-1-pentene, 3-methyl-1-butene, 4,4-dimethyl-1-pentene, 3-methyl-1-pentene, 4-methyl-1-hexene, 5-ethyl-1-hexene, 6-methyl-1-heptene, 1-hexene, 1-heptene, 1-octene, 1-nonene, and 1-decene.

9. The particulate plug of claim 1, wherein the hydrophobic polymer/fatty acid blend comprises a hydrophobic polymer selected from copolymers comprising monomers selected from the group consisting of ethylene, propylene, 1-butene, 4-methyl-1-pentene, 3-methyl-1-butene, 4,4-dimethyl-1-pentene, 3-methyl-1-pentene, 4-methyl-1-hexene, 5-ethyl-1-hexene, 6-methyl-1-heptene, 1-hexene, 1-heptene, 1-octene, 1-nonene, and 1-decene.

10. The particulate plug of claim 1, wherein the hydrophobic polymer/fatty acid blend comprises a hydrophobic polymer or copolymer selected from the group consisting of polyethylene, polystyrene, polyvinylchloride, polytetrafluorethylene, polydimethylsiloxane, polyesters, polyurethanes, acrylic, and epoxy.

11. The particulate plug of claim 1, wherein the hydrophobic polymer has an average MW of about 10,000, about 20,000, about 50,000, about 100,000, about 200,000, about 210,000, about 220,000, about 230,000, about 240,000, about 250,000, about 260,000, about 270,000, about 280,000, about 290,000, about 300,000, about 300,000, or greater than 300,000.

12. The particulate plug of claim 1, wherein the hydrophobic polymer/fatty acid blend comprises a fatty acid selected from a fatty acid having the structure: $CH_3(CH_2)_nCO_2H$, wherein n is 2 to 24.

13. The particulate plug of claim 12, wherein n is 14 to 20.

14. The particulate plug of claim 13, wherein n is 16.

15. The particulate plug of claim 1, wherein the fatty acid is selected from the group consisting of caprylic acid, capric acid, lauric acid, myristic acid, palmitic acid, stearic acid, arachidic acid, behenic acid, lignoceric acid, and cerotic acid.

16. The particulate plug of claim 1, wherein the fatty acid is selected from the group consisting of Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, and Docosahexaenoic acid.

17. The particulate plug of claim 1, wherein the fatty acid is selected from a fatty acid having a melting point greater than 70° C.

18. The particulate plug of claim 1, wherein the weight-to-weight percentage of fatty acid is at least 5% to at least 95%.

19. The particulate plug of claim 18, wherein the weight-to-weight percentage of fatty acid is at least 20% to at least 80%.

20. The particulate plug of claim 18, wherein the weight-to-weight percentage of fatty acid is about 25%.

21. The particulate plug of claim 18, wherein the weight-to-weight percentage of fatty acid is about 50%.

22. The particulate plug of claim 18, wherein the weight-to-weight percentage of fatty acid is about 75%.

23. The particulate plug of claim 1, wherein the microparticles have a dimension of 5 μm to about 50 μm.

24. The particulate plug of claim 1, wherein the microparticles have a dimension of 50 μm to about 100 μm.

25. The particulate plug of claim 1, wherein the microparticles have a dimension of 100 μm to about 500 μm.

26. The particulate plug of claim 1, wherein the microparticles have a dimension of 500 μm to about 1000 μm.

27. The particulate plug of claim 1, wherein the microparticles have a dimension of 1,000 μm to about 10,000 μm.

28. A particulate plug for removing a preservative from a solution, suspension, or emulsion comprising a drug, the particulate plug comprising microparticles of a fatty acid, wherein the microparticles form a particulate plug capable of being fitted an outlet of a container for the solution, emulsion, or suspension, wherein the particulate plug selectively removes a preservative from the solution, emulsion, or suspension.

29. The particulate plug of claim 28, wherein the fatty acid is stearic acid.

* * * * *